United States Patent
Abbott et al.

(10) Patent No.: US 7,807,348 B2
(45) Date of Patent: Oct. 5, 2010

(54) OPTICAL IMAGING OF NANOSTRUCTURED SUBSTRATES

(75) Inventors: Nicholas Lawrence Abbott, Madison, WI (US); Paul F. Nealey, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 865 days.

(21) Appl. No.: 10/102,540

(22) Filed: Mar. 20, 2002

(65) Prior Publication Data

US 2003/0180966 A1     Sep. 25, 2003

(51) Int. Cl.
*G01N 33/00* (2006.01)
(52) U.S. Cl. .................. 435/6; 422/82.05; 422/82.08; 436/5; 436/501; 436/164; 436/166; 436/172
(58) Field of Classification Search .............. 436/5, 436/501, 164, 166, 172, 527, 525; 422/82.05, 422/82.08
See application file for complete search history.

(56) References Cited

U.S. PATENT DOCUMENTS

| 4,597,942 A | 7/1986 | Meathrel |
| 4,628,037 A | 12/1986 | Chagnon et al. |
| 4,725,669 A | 2/1988 | Essex et al. |

(Continued)

FOREIGN PATENT DOCUMENTS

DE          3617710 A1    12/1986

(Continued)

OTHER PUBLICATIONS

Ennulat, R. D. et al., "Thermal Radiography Utilizing Liquid Crystals," *Molecular Crystals and Liquid Crystals*, vol. 13, pp. 149-164, 1971; published by Gordon and Breach Science Publishers (United Kingdom).

(Continued)

*Primary Examiner*—Sam P Siefke
(74) *Attorney, Agent, or Firm*—Foley & Lardner LLP

(57) ABSTRACT

A method of imaging phenomena that occurs on a surface of a substrate includes contacting a fluid with a top surface of the substrate, and imaging phenomena that occurs on the top surface of the substrate by observing the substrate through polarized light in the absence of a liquid crystal after the liquid has contacted the top surface of the substrate. The top surface of the substrate has an anisotropic topography, and the wavelength of the polarized light is larger than the anisotropic topography of the top surface of the substrate. A method for determining the presence of an analyte in a sample includes: contacting a sample with a first portion of a top surface of a substrate that binds the analyte, the top surface of the substrate having an anisotropic topography; viewing the substrate through polarized light in the absence of a liquid crystal after it has been contacted with the sample; and determining whether the analyte is present in the sample by ascertaining whether the first portion of the top surface that was contacted with the sample appears different than it did before it was contacted with the sample. The wavelength of the polarized light is larger than the anisotropic topography of the top surface of the substrate. A difference in the appearance of the first portion of the top surface before and after contact with the sample indicates the presence of the analyte in the sample.

27 Claims, 9 Drawing Sheets

U.S. PATENT DOCUMENTS

| | | | |
|---|---|---|---|
| 4,812,556 | A | 3/1989 | Vahlne et al. |
| 4,909,630 | A | 3/1990 | Gawrisch et al. |
| 4,931,384 | A | 6/1990 | Layton et al. |
| 5,268,305 | A * | 12/1993 | Ribi et al. .................... 436/501 |
| 5,620,850 | A | 4/1997 | Bamdad et al. |
| 5,712,103 | A | 1/1998 | Leavitt et al. |
| 5,925,878 | A * | 7/1999 | Challener ................... 250/225 |
| 6,005,668 | A | 12/1999 | Held, III et al. |
| 6,060,327 | A | 5/2000 | Keen |
| 6,097,484 | A | 8/2000 | McIntosh et al. |
| 6,159,681 | A | 12/2000 | Zebala |
| 6,171,802 | B1 | 1/2001 | Woolverton et al. |
| 6,277,489 | B1 | 8/2001 | Abbott et al. |
| 6,284,197 | B1 | 9/2001 | Abbott et al. |
| 6,288,392 | B1 | 9/2001 | Abbott et al. |
| 6,306,594 | B1 | 10/2001 | Cozzette et al. |
| 6,383,815 | B1 | 5/2002 | Potyrailo |
| 6,383,816 | B1 | 5/2002 | Wirth et al. |
| 6,707,561 | B1 * | 3/2004 | Budach et al. .............. 356/521 |
| 6,951,715 | B2 * | 10/2005 | Cunningham et al. .......... 435/4 |

FOREIGN PATENT DOCUMENTS

| | | |
|---|---|---|
| EP | A 284 587 | 8/1988 |
| EP | 0 345 462 | 12/1989 |
| JP | 02311822 A2 | 12/1990 |
| JP | 02311824 A2 | 12/1990 |
| JP | 03010222 A2 | 1/1991 |
| JP | 03039932 A2 | 2/1991 |
| JP | 04057024 A2 | 2/1992 |
| JP | 04057025 A2 | 2/1992 |
| JP | 04284423 A2 | 10/1992 |
| JP | 05134257 A2 | 5/1993 |
| JP | 05134258 A2 | 5/1993 |
| JP | 06175136 A2 | 6/1994 |
| JP | 06194513 A2 | 7/1994 |
| JP | 06194662 A2 | 7/1994 |
| WO | WO 92/08978 | 5/1992 |
| WO | WO 99/63329 | 12/1999 |
| WO | WO 99/64862 | 12/1999 |
| WO | WO 01/61325 | 8/2001 |
| WO | WO 01/61357 | 8/2001 |

OTHER PUBLICATIONS

Novak, T. J. et al., "Use of Anisotropic Materials as Chemical Detectors," *Analytical Letters*, vol. 5, No. 3, pp. 187-192, 1972; published by Marcel Dekker, Inc. (New York, NY).

Poziomek, E. J. et al., "Use of Liquid Crystals as Vapor Detectors," *Mol. Cryst. Liq. Cryst.*, vol. 27, pp. 175-185, 1973: published by Gordon and Breach Science Publishers, Ltd. (Holland).

Saji, T. et al., "Reversible Formation and Disruption of Micelles by Control of the Redox State of the Head Group," *J. Am. Chem. Soc.*, vol. 107, pp. 6865-6868, 1985; published by the American Chemical Society (Washington, D.C.).

Heslot, F. et al., "Molecular Layering in the Spreading of Wetting Liquid Drops", *Nature*, vol. 338, pp. 640-642, 1989; published by Nature Publishing (New York, NY).

Pieranski P. et al., "Adsorption-Induced Anchoring Transitions at Nematic-Liquid-Crystal-Crystal Interfaces," *Phys. Rev. A.*, vol. 40, No. 1, pp. 317-322, Jul. 1, 1989; published by the American Physical Society (Washington D.C.).

Starkey, C.A. et al. "Evaluation of the Recombigen HIV-1 Latex Agglutination Test", *J. Clin. Microbiol.*, vol. 28, No. 4, pp. 819-822, Apr. 1990; published by the American Society for Microbiology (Washington D.C.).

Parish et al., "A Polyanion Binding Site on the CD4 Molecule, Proximity to the HIV-gp120 Binding Region," *The Journal of Immunology*, vol. 145, No. 4, pp. 1188-1195, Aug. 15, 1990; published by American Association of Immunologists, Inc. (Bethesda, MD).

Häussling, L. et al. "Biotin-Functionalized Self-Assembled Monolayers on Gold: Surface Plasmon Optical Studies of Specific Recognition Reactions", *Langmuir*, vol. 7, No. 9, pp. 1837-1840, Sep. 1991; published by the American Chemical Society (Washington, D.C.).

Jérôme, B., "Surface Effects and Anchoring in Liquid Crystals," *Rep. Prog. Phys.* vol. 54, pp. 391-452, 1991; published by IOP publishing Ltd. (United Kingdom).

Saji, T. et al., "Formation of Organic Thin Films by Electrolysis of Surfactants with the Ferrocenyl Moiety," *J. Am. Chem. Soc.*, vol. 113, pp. 450-456, 1991; published by the American Chemical Society (Washington, D.C.).

Schmitt, F.-J. et al., "Surface Plasmon Studies of Specific Recognition Reactions at Self-Assembled Monolayers on Gold," *Thin Solid Films*, vol. 210/211, pp. 815-817, 1992; published by Elsevier Sequoia.

Charych, D.H. et al., "Direct Colorimetric Detection of a Receptor-Ligand Interaction by a Polymerized Bilayer Assembly", *Science*, vol. 261, pp. 585-588, Jul. 30, 1993; published by the American Association for the Advancement of Science (Washington D.C.).

Cocchi, J.M. et al., "Comparison Between Direct Binding, Competition and Agglutination Assays in the Characterization of Polyclonal Anti-idiotypes Against Anti-HBs Human Monoclonal Antibodies," *Immunological Meth.*, vol. 160, pp. 1-9, 1993; Elsevier Science Publishers.

H. Weetall. "Preparation of Immobilized Proteins Covalently Coupled Through Silane Coupling Agents to Inorganic Supports," *Applied Biochemistry and Biotechnology*, vol. 41, pp. 157-188, 1993; published by Humana Press Inc. (Totowa, NJ).

Kuby, J., *Immunology*, Second Edition (1994), pp. 147-150; W.H. Freeman and Company (New York, NY).

Drawhorn, R. A. et al., "Anchoring of Nematic Liquid Crystals on Self-Assembled Monolayers Formed from Alkanethiols on Semi-transparent Films of Gold", *J. Phys. Chem.*, vol. 99, pp. 16511-16515, 1995; published by the American Chemical Society (Washington D.C.).

Gupta, V. K. et al., "Uniform Anchoring of Nematic Liquid Crystals on Self-Assembled Monolayers Formed from Alkanethiols on Obliquely Deposited Films of Gold," *Langmuir*, vol. 12, pp. 2587-2593, 1996; published by American Chemical Society (Washington D.C.).

Gupta, V. K. et al., "Azimuthal Anchoring Transition of Nematic Liquid Crystals on Self-Assembled Monolayers Formed from Odd and Even Alkanethiols," *Physical Review E*, vol. 54, No. 5, pp. R4540-R4543, Nov. 1996; published by The American Physical Society (Washington D.C.).

Yang, H. C. et al., "Molecular Interactions between Organized, Surface-Confined Monolayers and Vapor-Phase Probe Molecules. 8. Reactions between Acid-Terminated Self-Assembled Monolayers and Vapor-Phase Bases," *Langmuir*, vol. 12, pp. 726-735, 1996; published by American Chemical Society (Washington D.C.).

Gallardo, B. S. et al., "Ferrocenyl Surfactants at the Surface of Water: Principles for Active Control of Interfacial Properties," *Langmuir*, vol. 12, pp. 4116-4124, 1996; published by the American Chemical Society (Washington, D.C.).

Cornell, B.A. et al., "A Biosensor that uses Ion-Channel Switches," *Nature*, vol. 387, pp. 580-583, Jun. 5, 1997; published by Nature Publishing (New York, NY).

Lin, V. et al., "A Porous Silicon-Based Optical Interferometric Biosensor," *Science*, vol. 278, pp. 840-843, Oct. 31, 1997; published by the American Association for the Advancement of Science (Washington, D.C.).

Pan, J. J. et al., "Molecular Recognition and Colorimetric Detection of Cholera Toxin by Poly(diacetylene) Liposomes Incorporating Gm1 Ganglioside," *Langmuir*, vol. 13, No. 6, pp. 1365-1367, 1997; published by the American Chemical Society (Washington, D.C.).

Delamarche, E. et al., "Patterned Delivery of Immunoglobulins to Surfaces Using Microfluidic Networks," *Science*, vol. 276, pp. 779-781, May 2, 1997; published by the American Association for the Advancement of Science (Washington, D.C.).

Gupta, V. K. et al., "Optical Amplification of Ligand-Receptor Binding Using Liquid Crystals," *Science*, vol. 279, pp. 2077-2080, Mar. 27, 1998; published by the American Association for the Advancement of Science (Washington D.C.).

Ricco, A. J., "Surface Acoustic Wave Chemical Sensor Arrays: New Chemically Sensitive Interfaces Combined with Novel Cluster Analysis to Detect Volatile Organic Compounds and Mixtures," *Acc. Chem. Res.*, vol. 31, pp. 289-296, 1998; published by American Chemical Society (Washington D.C.).

Crooks, R. M. et al., "New Organic Materials Suitable for Use in Chemical Sensor Arrays," *Acc. Chem. Res.*, vol. 31, pp. 219-227, 1998; published by American Chemical Society (Washington D.C.).

Xia Y. N. et al., "Soft Lithography," *Angew. Chem. Int. Ed.*, vol. 37, pp. 551-575, 1998; published by Wiley Interscience (Germany).

Dancil, K. S. et al., "A Porous Silicon Optical Biosensor: Detection of Reversible Binding of IgG to a Protein A-Modified Surface," *J. Am. Chem. Soc.*, vol. 121 pp. 7925-7930, 1999; published by the American Chemical Society (Washington D.C.).

Naoka, M. et al., "Ferroelectric Liquid Crystal Alignment Films Utilizing Poly (DL amino acids) and Fibrous Proteins," *Kobunshi Ronbunshu*, vol. 56, No. 6, pp. 396-400, Jun. 1999.

Skaife, J. J. et al., "Quantitative Characterization of Obliquely Deposited Substrates of Gold by Atomic Force Microscopy: Influence of Substrate Topography on Anchoring of Liquid Crystals," *Chem. Mater.*, vol. 11, pp. 612-623, 1999; published by American Chemical Society (Washington D.C.).

Shah, R.R. et al., "Using Liquid Crystals To Image Reactants and Products of Acid-Base Reactions on Surfaces with Micrometer Resolution," *J. Am. Chem. Soc.*, vol. 121, pp. 11300-11310, 1999; published by American Chemical Society (Washington D.C.).

Kim, S-R. et al., "Orientations of Liquid Crystals on Mechanically Rubbed Films of Bovine Serum Albumin: A Possible Substrate for Biomolecular Assays Based on Liquid Crystals," *Anal. Chem.*, vol. 72, No. 19, pp. 4646-4653, Oct. 1, 2000; published by the American Chemical Society (Washington D.C.).

Power Point presentation regarding "Optical Detection and Amplification of Biomolecular Interactions Using Liquid Crystals," by Jeff Brake and Nicholas Abbott, dated Apr. 26, 2000. Presented at the University of Wisconsin-Madison, Madison, Wisconsin, on Apr. 26, 2000.

Niculescu, M. et al., "Redox Hydrogel-Based Amperometric Bienzyme Electrodes for Fish Freshness Monitoring," *Anal. Chem.*, vol. 72, pp. 1591-1597, 2000; published by American Chemical Society (Washington D.C.).

Shah, R. R. et al., "Coupling of the Orientations of Liquid Crystals to Electrical Double Layers Formed by the Dissociation of Surface-Immobilized Salts," *J. Phys. Chem. B*, vol. 105, pp. 4936-4950, 2001; published by American Chemical Society (Washington D.C.).

Japanese Office Action for JP 2003-578914 dated Jun. 8, 2009 (with English translation).

Canadian Office Action for Canadian Application No. 2,479,297 dated Jul. 2, 2009.

* cited by examiner

OPTICAL IMAGING OF NANOSTRUCTURED SUBSTRATES

GOVERNMENT RIGHTS

This invention was made with United States government support awarded by the following agency: NSF 0079983. The United States has certain rights in this invention.

FIELD OF THE INVENTION

The invention relates generally to methods and devices for imaging phenomena occurring on a nanostructured surface and more particularly relates to methods for detecting the presence of an analyte in a sample using a nanostructured substrate.

BACKGROUND OF THE INVENTION

Methods for detecting the presence of biological substances and chemical compounds in samples has been an area of continuous development in the field of analytical chemistry and biochemistry. Several types of assay currently exist for detecting the presence of target species or analytes in samples. Such methods include the radioimmunoassay (RIA) and the enzyme-linked immunosorbent assay (ELISA). Kuby, J., Immunology, W. H. Freeman and Company, New York, N.Y., pp. 147-150 (1991). Although ELISA and other immunosorbent assays are simple and widely used methods, they have several disadvantages. For example, labeled antibodies are often expensive, especially for assays requiring radioactive labels. Additionally, radioactive labels require special handling as radioactive materials. Furthermore, the labeling of a compound, may alter the binding affinity of antibody to analyte.

The direct detection of the binding of proteins and ligands has also been investigated using surface plasmon reflectometry (SPR). Schmitt, F.-J.; Haussling, L.; Ringsdorf, H.; Knoll, W., Thin Solid Films, 210/211, pp. 815 (1992); Haussling, L.; Ringsdorf, H. Langmuir, 7, pp. 1837 (1991). SPR is sensitive to changes in the index of refraction of a fluid near a thin metal surface that has been excited by evanescent electromagnetic waves. The binding of proteins to ligands may be detected by examining an increase in the resonance angle or intensity of signal. Typical angular resolution using this method is 0.005° allowing detection of sub-angstrom changes in adsorbed film thickness with SPR. However, care must be taken to ensure that the change in resonance angle is due to binding and not just a change in the bulk solution index of refraction. A thermally stable environment is required due to the dependence of the resonance angle on the index of refraction of the fluid. An increase in temperature from 25° C. to 26° C. in water amounts to a change in the index of refraction by 0.0001. This increase would result in the change in resonance angle of approximately 0.015° or roughly 0.2 nm in the observed height of a protein layer. This temperature stability requirement makes SPR unsuitable for most field applications. In addition, non-specific adsorption of molecules onto or near the sensor surface can lead to false changes in signal.

A method based on a porous silicon support that permits optical detection of the binding of specific proteins to ligands has also been disclosed. Lin, V.; Motesharei, K.; Dancil, K. S.; Sailor, M. J.; Ghadiri, M. R., Science, 278, pp. 840 (1997); Dancil, K. S.; Greiner, D. P.; Sailor M. J., J. Am. Chem. Soc., 121, pp. 7925 (1999). The porous areas are typically 1 to 5 µm deep and a few square micrometers to millimeters in area. Binding of streptavidin to biotinylated surfaces was initially found to reduce the index of refraction of the porous support, however this was later correctly attributed to surface oxidation.

The use of polymerized multilayer assemblies for the detection of receptor-ligand interactions has also been disclosed. Charych, D. H.; Nagy, J. O.; Spevak, W.; Bednarski, M. D., Science, 261, pp. 585 (1993); Pan, J. J.; Charych, D., Langmuir, 13, pp. 1365 (1997). Polydiacetylene multilayer films deposited by Langmuir-Blodgett technique change color from blue to red due to a conformational change in the polymer backbone. The response may be controlled and used for protein detection by attaching ligands to the multilayer.

Recently, several assay devices that utilize liquid crystals have been disclosed. For example, a liquid crystal assay device using mixed self-assembled monolayers (SAMs) containing octanethiol and biotin supported on an anisotropic gold film obliquely deposited on glass has recently been reported. Gupta, V. K.; Skaife, J. J.; Dubrovsky, T. B., Abbott N. L. Science, 279, pp. 2077-2079 (1998). In addition, PCT publication WO 99/63329 discloses assay devices using SAMs attached to a substrate and liquid crystal layer which is anchored by the SAM. PCT publication WO 01/61357 discloses a method for detecting pathogens using a liquid crystal and a substrate with a detection region that includes depressions which may be grooves. A blocking material such as bovine serum albumin may be used in conjunction with a binding agent such as an immunoglobulin to bind a pathogenic agent such as a virus or bacteria. A liquid crystal is used to detect whether the pathogenic agent is present in a sample.

Although many of the conventional assay methods described above work very well to detect the presence of target species, these methods are often expensive and usually require instrumentation and highly trained individuals. This makes such methods difficult to use in the field. Thus, a need exists for assay devices and systems which are easier to use and which allow for evaluation of samples in remote locations.

A need remains for convenient methods that may be used to detect the presence of analytes in a sample. A need also remains for a method that may be used to image phenomena that occur on a surface of a substrate.

SUMMARY OF THE INVENTION

The present invention provides devices and methods for imaging phenomena that occur on a surface. The invention also provides methods and devices for detecting the presence of an analyte in a sample.

A first aspect of the invention provides a method for imaging phenomena that occurs on a surface of a substrate. The method includes contacting a fluid with a top surface of the substrate and imaging phenomena that occurs on the top surface of the substrate by observing the substrate with polarized light after the fluid has contacted the top surface of the substrate. The top surface of the substrate has an anisotropic topography, and the wavelength of the polarized light is larger than the anisotropic topography of the top surface of the substrate.

In one embodiment of the method of imaging surface phenomena, the top surface of the substrate defines a plurality of grooves that have a width ranging from 1 nm to 1,000 nm and a depth ranging from 1 nm to 5,000 nm. In such embodiments, the grooves are separated by a distance ranging from 1 nm to 5,000 nm. In such embodiments, the wavelength of the light used to illuminate the sample is larger than the dimensions of the grooves. In other embodiments of the method for imaging phenomena that occurs on the surface of a substrate, the width of the grooves defined by the top surface of the substrate ranges from 10 nm to 400 nm. In still other embodiments, the depth of the grooves defined by the top surface of the substrate ranges from 10 nm to 400 nm. In still other embodiments, the grooves defined by the top surface of the substrate are separated by a distance ranging from 10 nm to 400 nm. In some embodiments, the grooves may be parallel.

The invention further provides methods for imaging phenomena that occurs on the surface of a substrate in which the substrate comprises a polymer. In other embodiments, the substrate comprises polyurethane. In yet other embodiments, the substrate includes a support such as a glass slide or glass plate.

In other embodiments of the method for imaging phenomena that occurs on the surface of a substrate, the top surface of the substrate is coated with a metal such as gold or silver. In some such embodiments, the metal coated on the surface of the substrate has a thickness ranging from 1 nm to 500 nm while in other embodiments, the thickness of the metal ranges from 5 nm to 300 nm. In still other such embodiments, the substrate further includes a layer of titanium underlying the gold or silver.

In some methods for imaging phenomena that occurs on the surface of a substrate, the substrate is observed using a polarizer and an analyzer after the fluid has contacted the top surface of the substrate. In other embodiments, the substrate is observed using a polarizer and an analyzer where the analyzer is configured so that it ranges from a crossed configuration to a configuration within 10° of a crossed configuration. In other embodiments, the substrate is observed using a polarizer and an analyzer where the analyzer is configured so that it ranges from a crossed configuration to a configuration within 2° of a crossed configuration. In still further such embodiments, the analyzer is configured so that it ranges from a crossed configuration to within 1° of a crossed configuration. In still other embodiments, the analyzer is configured so that it ranges from 0.5° from a crossed configuration to 5° from a crossed configuration. In some embodiments, the substrate is observed using a polarized light microscope after the fluid has contacted the top surface of the substrate.

The invention also provides a method for determining the presence of an analyte in a sample. The method includes: contacting the sample with a first portion of a top surface of a substrate that binds the analyte; viewing the substrate using polarized light in the absence of a liquid crystal after it has been contacted with the sample; and determining whether the analyte is present in the sample by ascertaining whether the first portion of the top surface that was contacted with the sample appears different than it did before it was contacted with the sample. The wavelength of the polarized light is larger than the anisotropic topography of the top surface of the substrate. A difference in the appearance of the first portion of the top surface before and after contact with the sample indicates the presence of the analyte in the sample. In some embodiments, the method further includes removing the sample from the top surface of the substrate before the substrate is viewed using polarized light. In other embodiments, the top surface of the substrate defines a plurality of grooves that have a width ranging from 1 nm to 1,000 nm and a depth ranging from 1 nm to 5,000 nm. In such embodiments, the grooves are separated by a distance ranging from 1 nm to 1,000 nm.

In one embodiment of the method of determining the presence of an analyte in a sample, the substrate includes a polymer such as polyurethane. In one such embodiment, the polymer is a molded polymer such as molded polyurethane. In some embodiments, the substrate includes a glass support.

In another embodiment of the method of determining the presence of an analyte in a sample, the first portion of the top surface of the substrate comprises a receptor molecule that binds the analyte. In yet other embodiments of the method of determining the presence of an analyte in a sample, the substrate includes a metal coated on a top surface of a polymer, and the receptor species is deposited over a self-assembled monolayer, such as a self-assembled monolayer formed from an organosulfur compound, on the top surface of the metal. In some such embodiments, the metal is silver or gold, and the thickness of the metal coating ranges from 2 nm to 400 nm, from 5 nm to 200 nm, or from 10 nm to 100 nm. In other embodiments, the organosulfur compound is a compound having the formula $HS(CH_2)_mCO_2H$ or $HS(CH_2)_nCH_3$ or a mixture thereof where m and n are integers having a value of 6, 7, 8, 9, 10, 11, 12, 13, 14, 15, 16, 17, or 18. In still other embodiments, the organosulfur compound is a compound of formula $HS(CH_2)_mCO_2H$ where m is an integer having a value such as those described above. In still other embodiments, the organosulfur compound is a hydroxy terminated organosulfur compound such as an alcohol or ethylene glycol terminated organosulfur compound. In still other embodiments, a metal such as gold or silver is coated on top of a layer of an adhesion promoting material such as titanium.

In other embodiments of the method for determining the presence of an analyte in a sample, the substrate includes a blocking layer. In some such embodiments, the blocking layer is an albumin such as bovine serum albumin.

In still other embodiments of the method for determining the presence of an analyte in a sample, the top surface of the substrate defines grooves having a width ranging from 10 nm to 400 nm and a depth ranging from 10 nm to 400 nm. In such embodiments, the grooves may be separated by a distance ranging from 10 nm to 400 nm. In some such embodiments, the grooves are parallel. In some embodiments in which the top surface of the substrate defines groves, the method includes flowing the sample through the grooves in the top surface of the substrate.

In some embodiments, the analyte is a molecule, an ion, a biological entity, a protein, an assembly of proteins, a virus, a prokaryotic organism, a eukaryotic organism, DNA, RNA, a fragment of DNA, a fragment of RNA, or a peptide. In other embodiments of the method for determining the presence of an analyte in a sample, the analyte is a protein, a virus, a bacteria, DNA, RNA, a fragment of DNA, a fragment of RNA, or a peptide.

In still other embodiments of the method for determining the presence of an analyte in a sample, the receptor species is a peptide, a polypeptide, a fragment of RNA, a fragment of DNA, biotin, avidin, a sugar, a polysaccharide, an immunoglobulin, a fragment of an immunoglobulin, or a metal complex such as Ni(II) nitrilotriacetate.

In still other embodiments of the method for determining the presence of an analyte in a sample, ascertaining whether the first portion of the top surface that was contacted with the sample appears different that it did before it was contacted with the sample includes comparing the first portion of the top surface that was contacted with the sample with a second portion of the substrate that did not contact the sample.

In still other embodiments of the method for determining the presence of an analyte in a sample, the first portion of the top surface of the substrate includes a first receptor molecule, and a second portion of the top surface of the substrate comprises a second receptor molecule. In such embodiments, the first receptor molecule binds to a first analyte species and the second receptor molecule binds to a second analyte species that is different than the first analyte species. In some such embodiments, the top surface of the substrate comprises a plurality of different receptor molecules.

In still other embodiments of the method for determining the presence of an analyte in a sample, the sample is a flowing stream that continuously contacts the first portion of the top surface of the substrate, and the substrate is used to continuously monitor the flowing stream.

In another aspect, the invention provides a method of detecting an analyte in a sample. The method includes: contacting a sample with a first portion of a top surface of a substrate that binds an analyte, the top surface of the substrate having an anisotropic topography and a metal coating; irradiating the substrate with light comprising a wavelength ranging from 600 nm to 850 nm before and after the sample has contacted the substrate; taking a first absorbance measurement of the light transmitted through the substrate before the sample has contacted the substrate; taking a second absorbance measurement of the light transmitted through the substrate after the sample has contacted the substrate; and determining whether there is a difference between the first and second absorbance measurements. The anisotropic topography of the top surface of the substrate is smaller than 600 nm. A difference between the first and second absorbance measurements indicates the presence of the analyte in the sample.

In one embodiment that includes taking absorbance measurements, the top surface of the substrate defines a plurality of grooves. The grooves have a width ranging from 1 nm to 1,000 nm and a depth ranging from 1 nm to 5,000 nm. In such embodiments, the grooves are separated by a distance ranging from 1 nm to 5,000 nm. In other such embodiments, the grooves defined by the top surface of the substrate have a width ranging from 10 nm to 400 nm and a depth ranging from 10 nm to 400 nm, and the grooves are separated by a distance ranging from 10 nm to 400 nm. In some embodiments, the grooves are parallel. In still other such embodiments, the substrate is irradiated with polarized light, that is, in one embodiment, perpendicular to the grooves.

In other embodiments that includes taking absorbance measurements, the metal of the metal coating is silver or gold.

In still other embodiments that includes taking absorbance measurements, the metal coating has a thickness ranging from 5 nm to 300 nm, from 30 nm to 120 nm, or from 50 nm to 70 nm.

In yet other embodiments that includes taking absorbance measurements, the top surface of the substrate further includes a receptor molecule that binds to the analyte. In still further embodiments, the top surface of the substrate includes a blocking layer, such as, in one embodiment, a serum albumin such as, bovine serum albumin.

Further objects, features and advantages of the invention will be apparent from the following detailed description when taken in conjunction with the accompanying drawings.

DETAILED DESCRIPTION OF THE INVENTION

Figure 1A:
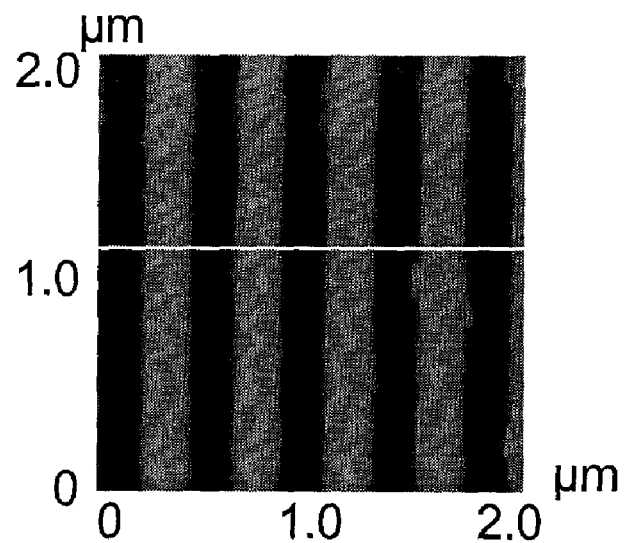
FIG. 1A is a two dimensional AFM (contact mode) scanned image of the SWG (sub-wavelength grating) structure of a polyurethane replica on a glass substrate.
Figure 1B:
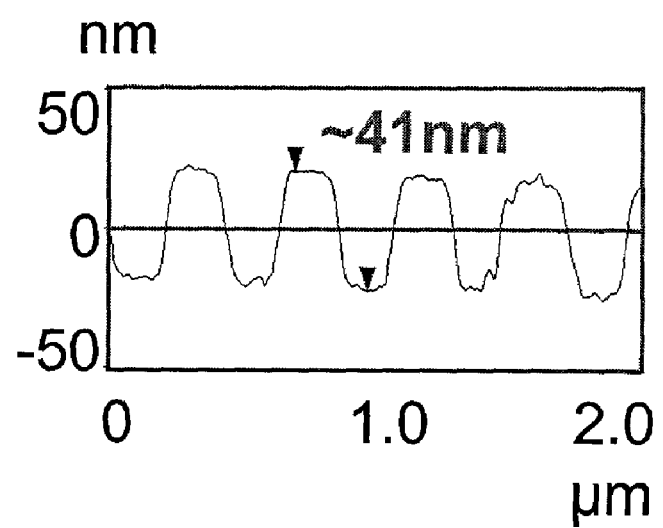
FIG. 1B is a cross-sectional profile representation of the scanned AFM image of FIG. 1A corresponding to the white line in FIG. 1A.

The term "AFM" refers to atomic force microscopy.
The term "SWG" refers to subwavelength grating.
The term "BSA" refers to bovine serum albumin.
The term "PBS" refers to phosphate buffered saline.
The term "SAM" refers to self-assembled monolayer.

All ranges recited herein include all combinations and subcombinations included within that range's limits. For example, a range of from about 5 nm to about 200 nm includes ranges of from 5 nm to 100 nm, of from 10 nm to 200 nm, of from 10 nm to 100 nm, of from 5 nm to 50 nm, of from 10 nm to 50 nm, of from 12 nm to 47 nm, of from 5 nm to 47 nm, of from 100 nm to 200 nm, of from 20 nm to 90 nm, and measurements of and about 5 nm, of and about 10 nm, of and about 20 nm, of and about 12 nm, of and about 47 nm, of and about 50 nm, of and about 60 nm, of and about 70 nm, of and about 100 nm, and of and about 150 nm etc. Furthermore, one skilled in the art will recognize that any listed range can be easily recognized as sufficiently describing and enabling the same range being broken down into at least equal halves, thirds, quarters, fifths, tenths, etc. As non-limiting examples, each range discussed herein can be readily broken down into a lower third, middle third, and upper third, and can be broken down into a lower half and an upper half.

The term "about" as used herein in conjunction with a number refers to a range of from 90% to 110% of that number. For example a width of about 50 nm refers to a width of from 45 nm to 55 nm.

Subwavelength gratings (SWGs) of isotropic materials possess anisotropy called form birefringence. Born, M.; Wolf, E., *Principles of Optics: Electromagnetic Theory of Propagation, Interference and Diffraction of Light*, Cambridge University Press, Cambridge (1999); Yariv, A.; Yeh, P., "Electromagnetic Propagation in Periodic Stratified media. II. Birefringence, Phase Matching, and X-ray Lasers", *J. Opt. Soc. Am.* 67, pp 438 (1977). The optical properties of a SWG depend on the structure of the grating and the indices of refraction of the materials comprising the grating structure (substrate and filling materials). Structures such as SWGs comprising nanometer-scaled grooves may be routinely fabricated using advanced lithographic techniques such as, but not limited to, e-beam writing as described by Moreau. Moreau, M. W., *Semiconductor Lithography: Principles and Materials*, Plenum Press, New York, N.Y., (1988). Replica molding of a hard SWG using polymeric materials allows the ready formation of polymeric replicas that include the SWG structure transferred from the hard SWG. Xia Y. N.; Whitesides, G. M., "Soft Lithography", *Angew. Chem. Int. Ed.*, 37, pp 551-575 (1998).

Surprisingly and unexpectedly, nanostructured substrates such as SWGs may be used to visualize a variety of surface phenomena employing polarized light microscopy. Although a liquid crystal may be employed to visualize the phenomena, none is required. A non-limiting example of such a surface phenomenon is the imaging of precursor liquid thin films that advance ahead of a bulk liquid in a drop of liquid spreading across a surface. Substrates coated with metals such as gold or silver may also be used to visualize surface phenomena employing either polarized light microscopy or by measurement and comparison of surface plasmon absorbance as light is transmitted through the substrate. Such metallized substrates may further include SAMs formed from materials such as nonfunctionalized alkanethiols and functionalized alkanethiols such as ω-terminated alkanethiols. SWGs coated with metals and comprising SAMs may also be used to visualize phenomena occurring on the surface of such modified nanostructured substrates. Nanostructured substrates such as those described above may additionally include a receptor species on a top surface that binds a particular analyte species. Additionally, such substrates may include a blocking layer which prevents non-specific adsorption on the top surface of the substrate. Such substrates allow the binding of an analyte species such as a protein to a complementary receptor species on the surface of the nanostructured substrate to be imaged. Therefore, such substrates provide useful devices for detecting the presence of an analyte in a sample.

Generally, the invention provides devices and methods for imaging phenomena that occur on the surface of a nanostructured substrate. The invention also generally provides methods and devices for detecting the presence of an analyte in a sample using a nanostructured substrate.

The optical properties of nanostructured substrates provide a broadly useful mechanism for enhancing contrast that may be employed to image phenomena that occur on a surface. The nanometer scale topography of a nanostructured substrate gives rise to optical birefringence or the resolution of light into two waves propagating with perpendicular vibration directions by an optically anisotropic medium. The penetration of any material such as, but not limited to, liquids, biomolecules, and viruses, into the topography on the surface of the nanostructured substrate modifies the birefringence and permits the location and presence of the material on the surface to be imaged and detected when using a polarizer and an analyzer.

A first method of imaging phenomena that occurs on a surface of a substrate includes contacting a fluid such as a liquid with a top surface of a substrate and then observing the substrate with polarized light such as by use of a polarizer and an analyzer. In some methods for imaging phenomena that occurs on the surface of a substrate, the substrate is observed using a polarizer and an analyzer after the fluid has contacted the top surface of the substrate. For example, the spreading of a droplet of a fluid such as an organic compound like hexadecane may be imaged using the method of the invention using a polarizer and an analyzer. In some embodiments, the substrate is observed using a polarizer and an analyzer where the analyzer is configured so that it ranges from a crossed configuration (where the angle between the analyzer and the polarizer is 90°) to a configuration within 10° of a crossed configuration i.e. the angle between the analyzer and the polarizer ranges from 80° to 100°. In other embodiments, the substrate is observed using a polarizer and an analyzer where the analyzer is configured so that it ranges from a crossed configuration to a configuration within 2° of a crossed configuration i.e. the angle between the analyzer and the polarizer ranges from 88° to 92°. In still further such embodiments, the analyzer is configured so that it ranges from a crossed configuration to within 1° of a crossed configuration i.e. the angle between the analyzer and the polarizer ranges from 89° to 91°. In still other embodiments, the analyzer is configured so that it ranges from 0.5° from a crossed configuration to 5° from a crossed configuration i.e. the angle between the analyzer and the polarizer ranges from 90.5° to 95° or from 85° to 89.5°. In some embodiments, the substrate is observed using a polarized light microscope after the fluid has contacted the top surface of the substrate. The substrate may also be observed while it is rotated between a polarizer and an analyzer.

The top surface of the substrate possesses anisotropic topography or a surface in which the topography or surface features in one azimuthal direction is different from that in one or more other azimuthal directions. The anisotropic topography gives rise to optical properties such as form birefringence or dichroism such as when the absorption of light on a metallized substrate depends on surface plasmon phenomena (See FIG. 7). In some aspects of the invention, the substrate has a nanotextured top surface that provides anisotropic topography. In one such embodiment, suitable substrates include those with a top surface that defines a plurality of grooves such as those shown in the AFM images of FIGS. 1A, 1B, 2A, 2B, 3A, and 3B. Generally, the dimensions of the grooves or other features providing the anisotropic topography in such embodiments, should be small compared to the wavelength of light used in imaging. While the light used to image surface phenomena and to detect analytes is typically visible light, light of longer wavelengths such as infrared light or shorter wavelengths such as ultraviolet light may also be employed. Thus, the width of the grooves in a suitable substrate typically ranges from 1 nm to 1,000 nm. In various embodiments of the present invention, the width of the grooves ranges from 2 nm to 800 nm, from 10 nm to 600 nm, from 10 nm to 400 nm, from 20 nm to 400 nm, and from 50 nm to 400 nm. The depth of the grooves in a suitable grooved substrate typically ranges from 1 nm to 5,000 nm. In various embodiments of the present invention, the depth of the grooves ranges from 2 nm to 800 nm, from 10 nm to 600 nm, from 10 nm to 400 nm, from 20 nm to 400 nm, and from 50 nm to 400 nm. The grooves in a suitable grooved substrate are typically separated by ridges such that the distance between the grooves ranges from 1 nm to 5,000 nm. In various embodiments of the present invention, the distance between the grooves in a substrate with a grooved top surface ranges from 2 nm to 800 nm, from 10 nm to 600 nm, from 10 nm to 400 nm, from 20 nm to 400 nm, and from 50 nm to 400 nm. The grooves in substrates such as those described above are parallel to one another in one embodiment of the invention. In some such embodiments, the grooves may be rectangular or square. In other embodiments, the grooves may be curved so that they have arcuate structure and may define ellipsoidal or circular depressions. In still other such embodiments, the grooves may be sinusoidal. In other embodiments, the top surface of the substrate defines a plurality of curved or parallel ridges that project up from the top surface of the substrate and which possess dimensions providing anisotropic topography. Such embodiments include those where the top surface of the substrate includes ellipsoidal or circular protrusions or parallel protrusions the latter of which may be formed using aligned rods. In still other embodiments, the top surface of the substrate may include anisotropic particles that provide anisotropic topography to the substrate surface.

An analyte with dimensions that are larger than the width of the grooves will not be able to fit into or penetrate the grooves in the top surface of a grooved substrate. For this reason, grooved substrates of the present invention may be used to determine the size of various analytes. A series of substrates with different groove widths may thus be used to determine the specific size of a particular analyte species in one embodiment of the invention. The grooves of grooved substrates may also be used to deliver a sample to the specific grooves in the top surface of a substrate as described below.

Suitable substrates for use in the practice of the invention may be formed from a number of materials. Examples of such materials include metals such as, but not limited to, gold, silver, copper, and nickel; inorganic glasses; and polymers. In one embodiment, polymers are particularly suitable for use in substrates of the present invention. Examples of suitable polymers include, but are not limited to, polystyrene, polymethylmethacrylate, polycarbonate, polycyanoacrylate, polyurethane, and polyimides. In one embodiment of the invention, the substrate is made of polyurethane which may be molded or formed using replica molding techniques. In one embodiment, the substrate includes a polymer such as polyurethane on a support such as a glass slide or plate. In other embodiments, the substrate comprises a material that is readily deformable. In such embodiments, mechanical deformation of the substrate produces a change in the retardation that is readily visualized. Mechanical stresses that lead to the deformation of the substrate may include binding events such as the binding of a cell to the substrate. Substrates may also be formed of materials such as polymers or hydrogels that swell or shrink when exposed to various solutions. For example, a substrate may be formed of poly(dimethylsiloxane) which swells upon absorption organic vapors.

The substrate may be produced using various manufacturing processes. In one suitable process, a mold is formed employing conventional micromachining processes, e.g., in a silicon workpiece, which then has a liquid polymer applied to it which is subsequently solidified. Mechanical embossing of a polymer similar to that used in the production of compact discs and holographic gratings may also be used. A hot, hard master may be pressed into a polymer sheet heated to near its glass transition temperature, transferring the relief in the master to the polymer. In such a process, the polymer is typically cooled below its glass transition temperature before removal of the master. Substrates may also be prepared using photopolymerization techniques. Suitable substrates may also be formed from masters using replica molding techniques such that in some embodiments, the substrate is a molded polyurethane replica on a glass support. In one method for preparing a substrate, a silicon or other master is used to form a polydimethylsiloxane (PDMS) or other elastomeric replica. Preferably, a fluorine-containing compound such as a fluorinated silane such as tridecafluoro-1,1,2,2-tetrahydrooctyl trichlorosilane is applied to the surface of the silicon master prior to making the elastomeric replica such that removal of the elastomeric replica is easier. The elastomeric replica is then preferably used as a master to form a replica from a thermally-curing material such as, but not limited to epoxide or more preferably from an ultraviolet-curing material such as, but not limited to polyurethane, polycyanoacrylate, or polystyrene. Polyurethane is an especially suitable material for use in forming such a polymeric replica.

The top surface of a substrate may include a coating of an inorganic material. Suitable inorganic materials include silicon oxides, metal oxides, metals, and combinations of these. An inorganic material such as a metal may be coated on a polymeric replica using vacuum deposition techniques. Silver and gold are examples of metals that are particularly suitable for use in manufacturing coated substrates. In metal-coated nanostructured substrates, the thickness of the metal coating in the substrate typically ranges from 2 nm to 500 nm, from 2 nm to 400 nm, from 5 nm to 200 nm, or from 10 nm to 100 nm. An obliquely deposited gold or silver surface may overlie a surface of titanium or other adhesion promotion material deposited on a top surface of the substrate. The use of an adhesion promoting material such as titanium provides better adhesion when metals such as gold or silver are deposited on top of it. However, the use of titanium or other adhesion-promoting materials is not required to prepare metal-coated substrates of the invention. If an adhesion promoting material is used, the material is typically present at a thickness ranging from 1 nm to 50 nm, from 2 nm to 30 nm, or from 3 nm to 10 nm. In some embodiments, approximately 3 nm of Ti is deposited on the top surface of a polymer having a nanostructured top surface. Gold is then deposited on top of the Ti to provide a gold coated nanostructured substrate with a gold thickness ranging from 12 nm to 47 nm and a titanium thickness of approximately 3 nm.

A substrate that includes a metal coating such as a gold or silver coating may be treated with various compounds that are chemisorbed onto the surface of the metal. For example, an organosulfur compound such as a compound with a sulfhydryl (—SH) or disulfide group will bind to the surface of a metal such as gold or silver forming a SAM. This provides a simple method for modifying the surface of a substrate. Suitable organosulfur compounds include nonfunctional alkanethiols such as compounds having the formula HS—X—Y where X is a spacer group and Y is a group such as an alkyl or aryl group. In such organosulfur compounds, X is a spacer group such as a substituted or unsubstituted alkyl chain, a substituted or unsubstituted aryl group, a substituted or unsubstituted alkylaryl chain, a perfluoroalkyl chain, or a perfluoroaryl group. Disulfides corresponding to such alkanethiols may also be used to treat metal surfaces to form SAMs. An example of a nonfunctional alkanethiol includes $HS(CH_2)_nCH_3$ where n is an integer having a value of 6, 7, 8, 9, 10, 11, 12, 13, 14, 15, 16, 17, or 18. Other suitable organosulfur compounds include compounds of the formula HS—X—Z where X is a spacer group such as those set forth above and Z is a functional group such as, but not limited to —$CO_2H$, —OH, —$CF_3$, —$SO_3H$, —$(N(alkyl)_3)^+$, —$NH_2$, —$(OCH_2CH_2)_qOH$, alkoxy groups, aryloxy groups, an aldehyde group, a ketone group, a sulfhydryl group, a sulfonyl halide, an acid halide group, a substituted or unsubstituted ferrocene group, an alkene group, an epoxide group, a diene group, biotin, a sugar, a low molecule weight receptor such as a benzenesulfonamide group, a quinone, or an initiator site for polymerizations where q is an integer selected from 1, 2, 3, 4, 5, 6, 7, 8, 9, or 10. Examples of such suitable organosulfur compounds include ω-terminated alkanethiols such as compounds having the formula $HS(CH_2)_mCO_2H$ where m is an integer with a value of 6, 7, 8, 9, 10, 11, 12, 13, 14, 15, 16, 17, or 18. Examples of other such suitable organosulfur compounds include hydroxy-terminated compounds such as, but not limited to alcohols of formula $HS(CH_2)_mOH$ and ethylene glycol terminated compounds such as, but not limited to, compounds of formula $HS(CH_2)_pO(CH_2CH_2O)_rCH_2CH_2OH$ where m has the values described above, p is an integer having a value of 2, 3, 4, 5, 6, 7, 8, 9, 10, 11, 12, 13, 14, 15, or 16, and r has a value of 0, 1, 2, 3, 4, 5, or 6. Examples of other such suitable organosulfur compounds include alkoxy- and aryloxy-terminated compounds such as compounds of formula HS—X—O—W where X is a spacer group such as those described above and W is an alkyl group or an aryl group. Examples of alkoxy- and aryloxy-terminated organosulfur compounds include compounds of formula $HS(CH_2)_mO$—W and compounds of formula $HS(CH_2)_p O(CH_2CH_2O)_r CH_2CH_2O$—W where m, p, and r have the values described above and W is an aryl group or an alkyl group having from 1 to 6 carbon atoms. Metallized substrates may also be treated with mixtures of organosulfur compounds to produce substrates with mixed SAMs. Various other compounds will bind to the surface of a metal in a substrate of the present invention. Such compounds may have the formula $R^1$—V—$R^2$ where V is a group that chemisorbs to the surface of the metal and $R^1$ and $R^2$ are selected from alcohols, amines, phosphonates, and carboxylic acid groups. In such compounds, V may be selected from aliphatic chains, ethylene glycol, or amide, ester or ether bonds. Various compounds such as, but not limited to, silanes may also be used to functionalize or activate the surface of a substrate as described below. Such compounds provide simple methods for attaching receptors to the top surface of substrates for use in the present invention.

Substrates that include an organosulfur compound on a top surface may be prepared by immersing a metallized substrate in a solution containing an organosulfur compound with a sulfhydryl or disulfide group. Alternatively, a solution that includes the organosulfur compound or a mixture of organosulfur compounds may be dropped or poured onto the surface or otherwise contacted with the metallized top surface of the substrate. Alternatively, an organosulfur compound or a mixture of organosulfur compounds may be deposited on a metal top surface of a substrate as a vapor using vapor deposition techniques. The sulfhydryl (—SH) group of the organosulfur compound binds to the metal of the substrate thereby immobilizing the organosulfur compound on the surface of the substrate. In some embodiments, the organosulfur compound is present in an alcohol such as ethanol or methanol although other liquids may also be employed in accordance with the invention.

Generally, substrates for use in detecting the presence of an analyte in a sample include a surface to which the analyte is bound upon exposure. The top surfaces of substrates may be designed for non-specific adsorption of analyte species. For example, the top surface of a substrate may include a hydrophobic surface, and species that present positively or negatively charged groups in aqueous solution to attract charged analyte species. In various embodiments, substrates for use in detecting the presence of an analyte in a sample include a receptor species that specifically binds or interacts with the analyte. Examples of suitable receptor species include various biomolecule recognition agents, including peptides and polypeptides; RNA and DNA oligomers or fragments; biotin; avidin; sugars including mono- di- and polysaccharides; antibodies; FAB and FAB' or other fragments of antibodies such as, but not limited to, immunoglobulins, such as but not limited to, IgG; and small molecules (e.g., drugs) tethered to the surface of the substrate (permitting screening of small molecule/protein-virus interactions for drug research). The top surface of the substrate may also comprise a polymer material such as a functional polymer that includes a ligand that binds a virus or a reactive moiety that can be used to covalently attach a binding agent (e.g., an —SH group). Immunoglobulins including IgG, IgA, IgM, IgD, and IgE, and fragments of immunoglobulins are suitable receptor species, and IgG and fragments of IgG are especially suitable as receptor species. The receptors may also bind to prokaryotic and eukaryotic organisms to alter their presence and behavior (shape, migration, adhesion, and proliferation). For example, a suitable receptor may comprise the RGD tripeptide that binds integrins on cell surfaces and thus promotes cell adhesion to surfaces and subsequent proliferation.

The top surface of a nanostructured substrate may additionally be coated or covered with a layer of material that functions as a blocking layer to prevent nonspecific adsorption of viruses, bacteria, and biomolecules to the surface when they are not complementary to the receptor species. An exemplary blocking layer material comprises an albumin film such as a film of bovine serum albumin (BSA). The blocking layer may be formed from albumins derived from other animals or by immobilizing materials such as poly(ethyleneoxide) on the surface of the substrate. Zwitterionic polymers may also be used to reduce non-specific adsorption. The material of the substrate itself may also be selected to prevent non-specific adsorption. As a further non-limiting example, the polymer of the substrate may be derivatized using oligoethylene glycol strands to prevent non-specific adsorption. In accordance with one aspect of the invention, a receptor species on the surface of the substrate in or on the blocking layer specifically binds an analyte to be detected. A receptor species such as BSA may act as both a blocking layer and as a receptor species. For example, BSA blocks the non-specific adsorption of species such as anti-goat IgG, but is a specific receptor for anti-BSA IgG. The proper selection of a blocking layer and receptor species allows the substrates of the present invention to be used for the detection of a wide variety of specific analytes in a sample.

A receptor species may be immobilized on the surface of a substrate using various procedures for immobilizing compounds on the surfaces of solids. In one method, a receptor is physically adsorbed on the surface of a substrate. This is particularly suitable where the receptor is a protein. A blocking layer may then be added by subsequent immersion into a solution of an a albumin such as BSA or a solution of powdered milk. A receptor may also be covalently bonded or linked to the surface of a substrate by employing thiol or silane chemistry. For example, if using a metal-coated substrate such as a gold-coated substrate, a primary amine of a protein may be covalently linked to a carboxylic acid group of an acid-terminated alkanethiol bound to the surface of the metal. Alternatively, a sulfhydryl group of a dithiol may be used in combination with a heterobifunctional cross-linking agent such as, but not limited to, N-succinimidyl 3-(2-pyridyldithio)-propionate to form a covalent linkage to a primary amine group of a protein. The surface may then be blocked by immersing the surface in an albumin solution such as a BSA solution or a solution of powdered milk. If the receptor is a small molecule such as Ni(II) nitrilotriacetate, then it may be chemically modified to include a thiol group that binds directly to the gold. The surface may be blocked by coadsorption of an ethyleneglycol-terminated alkanethiol. In another method of immobilizing a receptor on a substrate surface, various silane chemistry may be employed. A primary amine such as, but not limited to, 3-aminopropyltriethoxysilane may be activated using an activating agent such as, but not limited to, disuccinimidyl suberate, and then reacted with the primary amine of a protein receptor. It will be evident to those skilled in the art, that there are many other approaches that may be used to immobilize receptors on surfaces and prepare substrates having blocking layers.

In one embodiment, a surface that promotes non-specific binding may be prepared by contacting the top surface of a gold coated polyurethane replica with a solvent that includes an organosulfur compound such as a droplet of ethanol containing 1 mM hexadecanethiol. The droplet may be contacted with the top surface for a period of 5 minutes at ambient temperatures, and then rinsed from the surface with copious amounts of ethanol. The replica may then be dried under a stream of an inert gas such as nitrogen. The resulting surface of the replica substrate is highly hydrophobic and non-specifically adsorbs a wide range of proteins.

A method for determining whether an analyte is present in a sample includes contacting the sample with a first portion of a top surface of a substrate of the invention. The top surface of the substrate includes a first portion that binds the analyte. Optionally, the top surface includes a receptor species that interacts with or binds one particular analyte or class of analytes. The sample is typically contacted with the top surface of the substrate for a period of time ranging from about 0.001 hours to about 10 hours. The sample may be a stream that continuously contacts the substrates so that the substrates may be used in applications such as in water quality control. The time that the sample contacts the substrate will vary depending on the concentration of the analyte in the sample. If the concentration of the analyte is in the millimolar (mM) or molar (M) range, then short contact times (seconds to minutes) will likely be sufficient. The contact time will also depend, in part, on the mechanisms of mass transport of the analyte to the surface. If convection is forced, such as by using microfluidic channels or by stirring or by ultrasonication, then the binding time required may be reduced compared to situations where delivery to the surface is purely diffusive. The binding time may also be accelerated by application of a constant or time and spatially varying electrical potential to metal-coated nanostructured substrates. The applied potential may cause migration of charged species, cause a force to act on species in solution such as by dielectrophoretic forces, or cause convection within the liquid by electrokinetic phenomena such as electroosmosis. When no convection or aid to mass transport is used, and the concentration of the analyte is in the femtomolar (fM) range, then it may be necessary to contact the substrate with the stream for many hours in order to detect the presence of a targeted species or class of species. Those skilled in the art will recognize, that magnetic beads may also be used to accelerate the delivery of targeted analytes to a nanostructured surface of a substrate.

In one embodiment, a sample to be analyzed may be contacted with a grooved substrate by flowing the sample along the grooves of the substrate. In such embodiments, a planar top plate may optionally be placed over the top surface of the substrate to confine the flow of the sample in and through the grooves of the substrate. Such embodiments effectively use nanofluidic delivery to bring the analytes to the sensing service of the substrate.

After the sample has contacted the top surface of the substrate for a suitable length of time to insure that a suitable amount of the analyte, if present, has been bound to a receptor species or the top surface of the substrate, the sample is typically removed from the top surface of the substrate. It will not always be necessary to remove the sample from the substrate prior to imaging. In some cases it may be desirable to leave the sample in contact with the substrate during the imaging process. If the sample is removed, then it may be removed using a second fluid to displace the sample from the substrate. In removing the sample using this method, a liquid may be used to displace the sample or alternatively a fluid such as air or nitrogen gas may be used to displace the sample. The sample may also be removed using vibration or by application of a mechanical force to the sample. For example, a sample may be removed from a substrate by tilting the substrate such that the sample drains away under the influence of gravity. Following removal of the sample from the top surface of the substrate, the substrate is typically rinsed with one or more solutions such as deionized water or other aqueous solutions, or with organic liquids such as, but not limited to an alcohol such as methanol or ethanol. After rinsing, the substrate is generally dried prior to visualization although wet substrates may also be viewed using polarized light in accordance with the present invention. A substrate may be dried by evaporation or by flowing a stream of a gas such as nitrogen, air, or argon over the sample.

After removing the sample from the top surface of the substrate and optionally rinsing and drying the substrate, in one embodiment the substrate is viewed through polarized light. For example, the substrate may be viewed through a polarized light microscope using cross polarizers. The presence of the analyte in the sample may be determined by comparing the optical appearance of the portion of the substrate that was contacted with the sample with another portion of the substrate that did not contact the sample. A difference in the optical appearance of the two portions indicates that the sample contained an analyte that binds to the receptor of the substrate. Alternatively, the presence of the analyte may be determined by incorporating a "control area" on the substrate that does not bind the analyte. An example of such an area includes one that does not include the receptor species. Comparison of the appearance of the control area to the analyte binding area will reveal whether or not the analyte is present. In another alternative method, a measurement of the absolute intensity of the surface prior to and after contact with the sample may be used in determining whether the analyte is present. In some embodiments, a liquid that has a refractive index significantly different from that of the analyte bound to the substrate may be utilized as an image-enhancing fluid. The presence of an image-enhancing fluid will maximize the optical contrast between the appearance of regions of the surface that include the targeted species and regions that do not. Preferred image enhancing fluids include air or nitrogen, although liquids may also be employed in this capacity.

The substrates of the present invention may be designed to detect more than one analyte or class of analytes in a sample. For example, a first receptor molecule capable of binding a first analyte species may be present on the top surface of a first portion of a substrate, and a different second receptor molecule capable of binding a second different analyte species may be present on the top surface of second portion of the substrate. Similarly, a plurality of different receptor molecules may be present in a plurality of different portions on the top surface of a substrate of the invention such that a plurality of different analytes may be detected in a sample using the methods of the present invention. Multiple receptors can be placed on the substrate using conventional spotting technologies that deliver small droplets of liquids to discrete areas of a surface. Alternatively, photolithographic methods can be used to pattern receptors on surfaces, such as those technologies used for preparing arrays of DNA on surfaces. Alternatively, microfluidic channels can be contacted with the surface of the replica and used to deliver receptors to spatially distinct regions of the surface.

A metal coated substrate may be connected to an external electrical circuit that includes a variable voltage and frequency power supply. The substrate may be immersed in an electrolyte solution along with a second electrode that serves as a counter electrode. Application of a potential difference between the counter electrode and the metal coated substrate creates an electric field in the solution. This electric field creates a force on charged molecules within the solution and causes theme to migrate towards the surface of the metal coated substrate. If the electric field is a DC field, then the migration will result from electrophoresis. However, even with uncharged objects, dielectric forces can be exerted by electric fields. If there exists a gradient in an electric field, then dielectrophoresis may cause target species to migrate towards an electrode. This migration can be manipulated by varying the frequency of the field. Application of a positive electrical potential to a metal coated substrate in a solution containing DNA will result in the migration of the DNA towards the metal coated substrate. Application of a negative electrical potential to a metal coated substrate in a solution at a pH that is lower than the pI of a protein dissolved in the solution will result in the migration of the protein towards the metal coated substrate.

Changes in the absorbance of light transmitted through substrates of the present invention may also be used to detect the presence of an analyte in a sample. Such changes in absorbance may be due to surface plasmon absorption phenomena. Various methods in which the absorbances are used may be employed to determine whether an analyte species is present in a sample. One method for detecting the presence of an analyte in a sample includes contacting a sample with a first portion of a top surface of a substrate that binds an analyte. The top surface of substrates for use in methods employing absorbance measurements such as surface plasmon absorbances should include anisotropic topography as described above and a metal coating such as a silver or gold coating. The anisotropic topography of the top surface of substrates for use in such methods should generally be smaller than the wavelength of light used to irradiate the substrate, and is generally less than 600 nm. The thickness of the metal coating in such applications typically ranges from 5 nm to 300 nm, from 30 nm to 120 nm, and from 50 to 70 nm in various embodiments. The substrate is irradiated with light that includes light of a wavelength ranging from 500 nm to 850 nm or more preferably from 600 nm to 850 nm before and after the sample has contacted the substrate. The light may include other wavelengths so long as it includes, as a component, light of a wavelength ranging from 500 nm to 850 nm or from 600 nm to 850. A first absorbance measurement is taken of the light transmitted through the substrate before the sample has contacted the substrate (See FIG. 7). A second absorbance measurement is taken of the light transmitted through the substrate after the sample has contacted the substrate. A comparison of the first and second absorbance measurements allows one to determine whether there is a difference between the measurements. A difference between the first and second absorbance measurements indicates the presence of the analyte in the sample because the presence of the analyte on the top surface of the substrate changes the absorbance of light transmitted through the substrate. As in embodiments where the retardation of the light is used to detect the presence of an analyte in a sample, the top surface of the substrate may include a receptor molecule that binds the analyte and may also include a blocking layer such as those described above.

In one embodiment of the method for detecting the presence of analytes using absorbance measurements, the substrate is a grooved substrate where the top surface of the substrate defines a plurality of grooves having a width ranging from 1 nm to 1,000 nm and a depth ranging from 1 nm to 5,000 nm, and the grooves are separated by a distance ranging from 1 nm to 5,000 nm. In other embodiments, the grooves have a width ranging from 10 nm to 400 nm and a depth ranging from 10 nm to 400 nm, and the grooves are separated by a distance ranging from 10 nm to 400 nm. The grooves may be curved, but are parallel in one embodiment. Although it is possible to use light that is not polarized in practicing the invention, in one embodiment, the substrate is irradiated with polarized light that is more preferably perpendicular to the direction of grooves defined in the top surface of the substrate as this has been found to maximize surface plasmon absorbance (see FIG. 7).

EXAMPLES

Materials

Fisher's Finest, Premium Grade glass microscope slides obtained from Fisher Scientific (Pittsburgh, Pa.) were used to manufactures substrates. Glass slides were cleaned prior to use by treating with "piranha solution" (70% $H_2SO_4$/30% $H_2O_2$). "Piranha solution" should be handled with extreme caution because it reacts violently with organic materials and should not be stored in closed containers. After cleaning for 1 hour at 80° C. in "piranha solution", the slides were rinsed well in deionized water, and dried under a stream of nitrogen. Prior to use, the clean glass slides were stored in an oven heated at 120° C. for at least 3 hours. Poly(dimethylsiloxane) (PDMS, Sylgard® 184, Dow Corning Co. (Midland, Mich.)) and polyurethane (PU, NOA61, Norland Products Inc. (New Brunswick, N.J.)) were used as thermally-curable or ultraviolet-curable polymers in forming polymer replicas. Bovine serum albumin (BSA, IgG free, lyophilized powder) was obtained from Sigma (St. Louis, Mo.) and used as received. Anti-BSA IgG and anti-goat IgG were also obtained from Sigma. Hexadecane was obtained from Aldrich (Milwaukee, Wis.). Tridecafluoro-1,1,2,2-tetrahydrooctyl trichlorosilane was obtained from Gelest (Tullytown, Pa.). The nematic liquid crystal 4-cyano-4'-pentylbiphenyl (5CB), manufactured by BDH, was purchased from EM industries (Hawthorne, N.Y.).

Formation of Master and Polyurethane Replica Nanostructured Substrates

As master substrates for replica molding, patterned silicon wafers (200 nm pattern and 50 nm depth) were prepared by e-beam writing and etching. Before molding the poly(dimethylsiloxane)(PDMS) prepolymer, the original silicon master was silanized by exposing it to fluorinated silane vapor to prevent the PDMS from sticking to the surface of the silicon master. This was accomplished under nitrogen using a glove box (model CC-40, Vacuum Atmospheres Co. (Hawthorne, Calif.)). First, the clean silicon master was attached to a support in a dessicator and suspended face down approximately 2 cm above a 3% (v/v) solution of fluorinated silane (tridecafluoro-1,1,2,2-tetrahydrooctyl trichlorosilane) in heavy mineral oil. Using a vacuum pump, the inner pressure of the dessicator was then adjusted to a pressure of about 0.1 Torr. After about 6 hours, the dessicator was filled with nitrogen, and the sample was removed. The presence of the fluorinated SAM was confirmed by measurement of the contact angle of water on a reference silicon wafer. The contact angle was measured using a Ramé-Hart model 100 contact angle goniometer (Mountain Lakes, N.J.). The measured contact angle of water on the fluorinated silicon wafer was over 110°.

Figure 8:
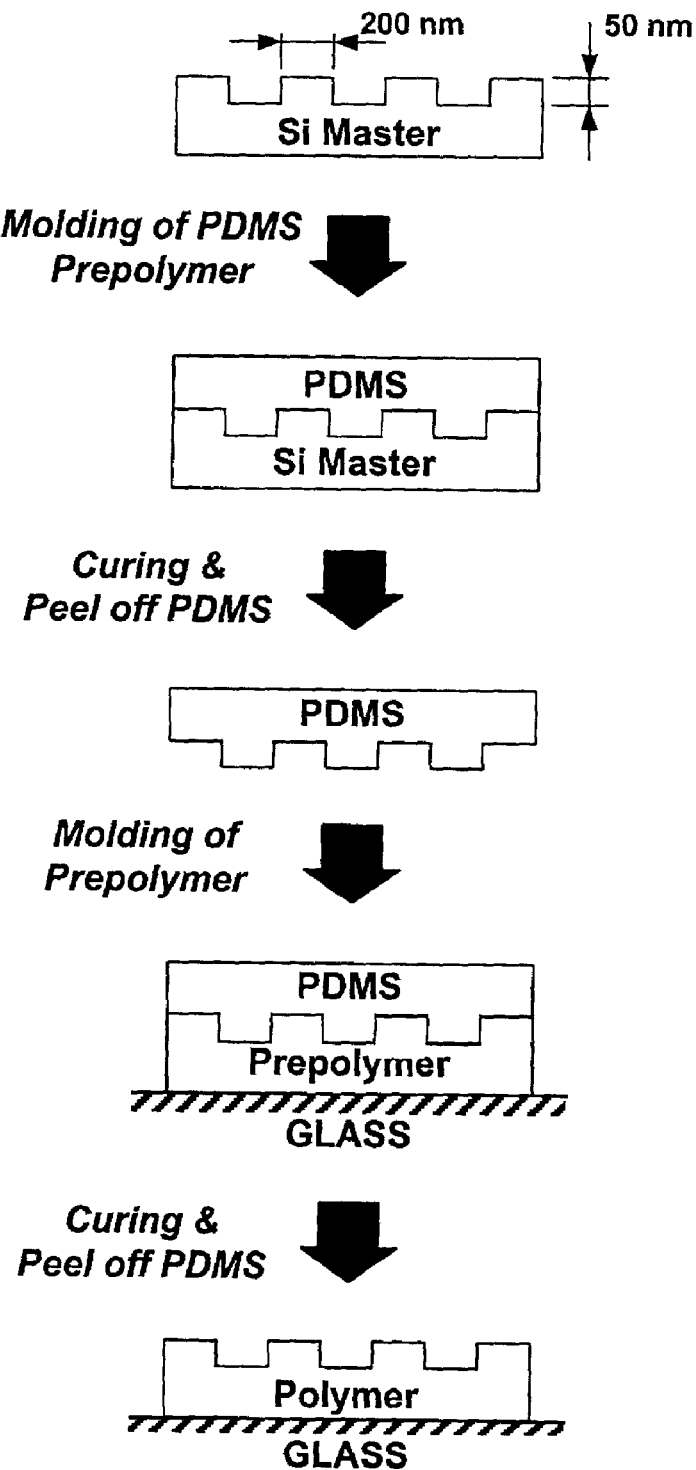
FIG. 8 is a schematic diagram showing how a polymeric substrate may be formed from a silicon master.

FIG. 8 schematically illustrates the procedure used for forming a PDMS master from a silicon master prepared as described above. FIG. 8 also illustrates how the PDMS master was used to form substrates from various polymers. Elastomers were used in the formation of masters from the silicon master because they can make conformal contact with surfaces over relatively large areas and because they can be released easily from rigid masters (low interfacial free energy of about 21.6 dyne/cm). Additionally, elastomers typically exhibit good chemical stability. Elastomeric PDMS replicas were fabricated by pouring a mixture of a liquid prepolymer of PDMS and a curing agent (10:1 by weight) over the patterned and fluorinated surface of the silicon master placed in a plastic petri dish. To remove entrained air bubbles in the PDMS prepolymer/curing agent mixture that resulted from the mixing and pouring procedure, the petri dish was placed in a vacuum oven for approximately 30 minutes at room temperature. The prepolymer mixture was then cured at 60° C. in a vacuum oven for 1 day. After curing, the PDMS replica was gently peeled away from the silicon master. Finally, the cured PDMS replica was rinsed with ethanol and dried under a gaseous stream of nitrogen.

Formation of Polyurethane Replicas from Elastomeric PDMS Master

Replication using elastomeric masters was found to increase the ease of separating the master and the replica, to protect the structures during separation, and to minimize damage to the master that may occur during the replication process. Various polymeric replicas were formed on a glass substrate as schematically illustrated in FIG. 8 using a PDMS master prepared as described above. To prepare replicas with UV-curable prepolymers leading to polyurethane, a PDMS master was first placed on a glass substrate, and approximately 100 μm thick spacer films (DuPont Films, Wilmington, Del.) were used to maintain a gap between the glass substrate and the PDMS master. Using a syringe, the liquid UV-curable prepolymer was injected between the PDMS master and the glass substrate which was then filled by capillary force on the hot plate (at about 60° C.). These prepolymers were cured with UV light (365 nm, UV crosslinker, Spectronics Co., Westbury, N.Y.) for 2 hours under nitrogen flow and aged overnight at 60° C. in an oven. After peeling the PDMS master off the surface of the replica, the PDMS master was cleaned with ethanol. A single PDMS master could be used to fabricate more than 10 polymeric replicas without any noticeable change in the replicated polymeric pattern as confirmed by atomic force microscopy (AFM), optical microscopy, and alignment of liquid crystals.

Formation of Metallized Nanostructured Substrates and Metallized Substrates with SAMs The polyurethane replicas formed as described above were mounted on the planetaries in an electron beam evaporator (TekVac, NJ). The evaporator was evacuated to a pressure of 0.0000001 Torr. The planetaries were rotated in an epicyclic manner during the sequential deposition of titanium and then gold. The thickness of the metals was measured using a quartz crystal microbalance mounted in the evaporator.

The metal coated substrates were functionalized with the carboxylic acid-terminated alkanethiol, $HS(CH_2)_{10}COOH$, by immersing the substrate in a 1 mM ethanolic solution of the organosulfur compound for 1 hour. The substrate was removed, rinsed with ethanol, and then dried under a stream of nitrogen.

Imaging of Nanostructured Substrates Using AFM

AFM images of the polyurethane replica nanostructured substrates were obtained using a digital Instruments Nanoscope III brand multimode scanning probe microscope(Santa Barbara, Calif.) operating in contact mode or tapping mode. Samples were imaged under ambient conditions using a cantilever made from silicon nitride (spring constant: 0.06 N/m) at a scan rate of 1.0 Hz with 512 sample points per line.

Figure 2A:
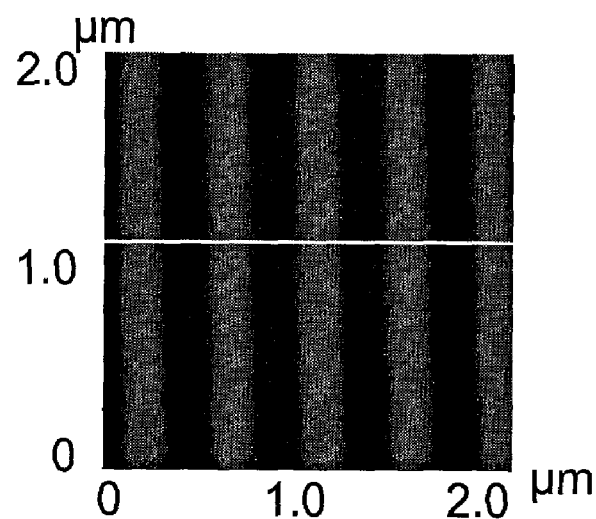
FIG. 2A is a two dimensional AFM (contact mode) scanned image of the SWG structure of a coated (12 nm Au on 3 nm Ti) polyurethane replica on a glass substrate.
Figure 2B:
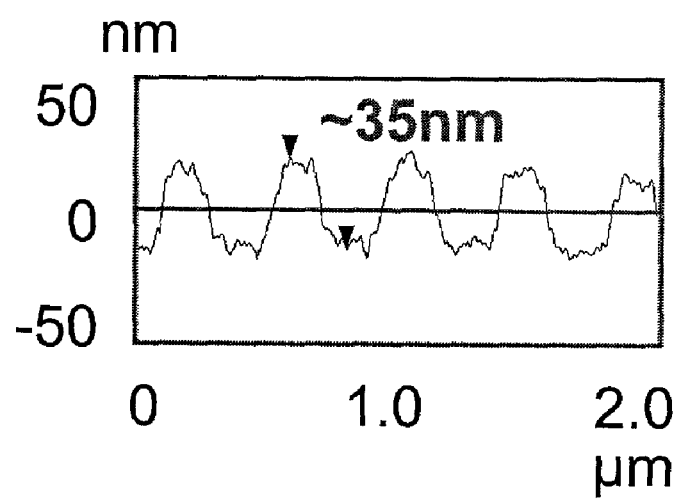
FIG. 2B is a cross-sectional profile representation of the scanned AFM image of FIG. 2A corresponding to the white line in FIG. 2A.
Figure 3A:
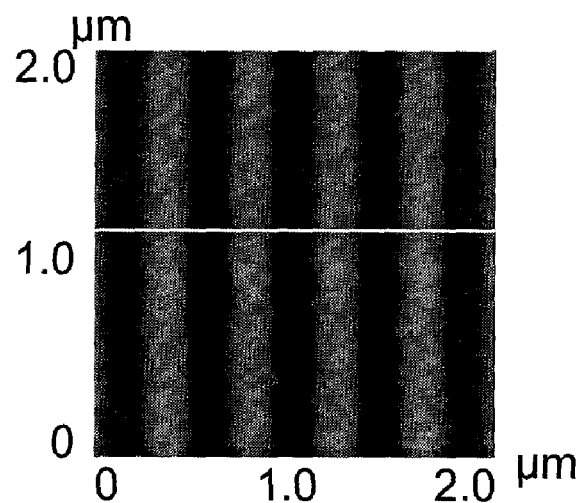
FIG. 3A is a two dimensional AFM (contact mode) scanned image of the SWG structure of a coated (47 nm Au on 3 nm Ti) polyurethane replica on a glass substrate.
Figure 3B:
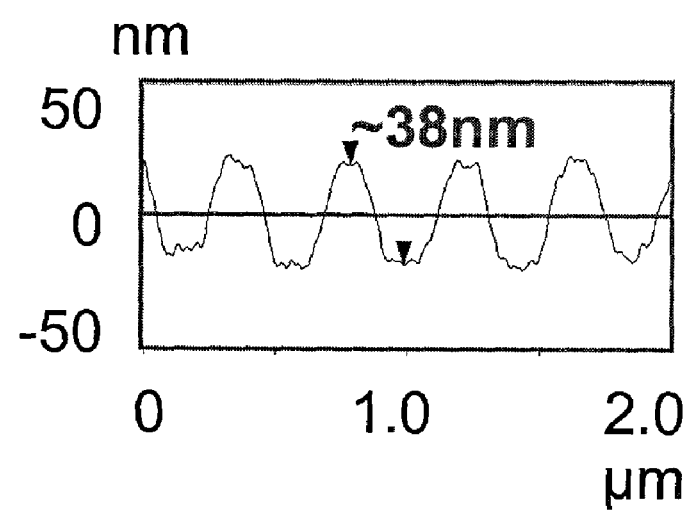
FIG. 3B is a cross-sectional profile representation of the scanned AFM image of FIG. 3A corresponding to the white line in FIG. 3A.

Polyurethane SWGs were prepared on glass supports using replica molding techniques as described above. A thin layer of a metal such as gold or silver was used to modify the anisotropic optical properties of the nanostructured substrate without changing the overall morphology of the SWG structure. The structure of a polyurethane replica nanostructured substrate and its gold-coated surface (gold deposited up to 50 nm thick using an e-beam evaporator) were evaluated using contact mode AFM, as shown in FIGS. 1A, 1B, 2A, 2B, 3A, and 3B. AFM images indicated that the overall structure of the SWG was not significantly altered by addition of the gold layer or the underlying adhesion-promoting titanium layer. Although the rectangular groove of the polyurethane replica without the gold coating shown in FIG. 1B did smooth out some as titanium and then gold were coated on the surface as shown in FIGS. 2B (12 nm Au on 3 nm Ti) and 3B (47 nm Au on 3 nm Ti), the general morphology of the substrate was not appreciably altered. No noticeable differences were observed with respect to groove shape, groove depth, or groove width when the structures imaged using contact mode AFM were compared with images obtained using noncontact-mode scanning employing a carbon nanotube probe.

Imaging of Nanostructured Substrates Using Microscopy

An Olympus® BX-60 brand polarized light microscope (Tokyo, Japan) was used to observe the polymeric polyurethane replica nanostructured substrates and the optical texture formed by light transmitted through the substrates. Images of the optical appearance of the nanostructured substrates were captured with an Olympus® C-2020 brand CCD camera (Olympus America Inc. (Melville, N.Y.)) that was attached to the polarized light microscope. The pictures were obtained using high quality mode (resolution of 1600×1200 pixels) at an aperture of f11 and a shutter speed of $\frac{1}{6}$ second for the observation of the polyurethane replica (microscope setting: light source of 100% of maximum intensity and 100% open aperture) whereas a shutter speed of $\frac{1}{320}$ second was used for observing the optical cells prepared from the polymeric replicas (microscope setting: light source of 50% of maximum intensity and 50% open aperture).

Analysis of Hexadecane on Surface of Nanostructured Substrates

A droplet of hexadecane was deposited on a substrate mounted on the rotation stage of an Olympus® BX60 brand polarized light microscope (Olympus (Tokyo, Japan). Images of the droplet of hexadecane were recorded using an Olympus® C-2020 brand CCD camera (Olympus America Inc. (Melville, N.Y.)) as demonstrated in FIGS. 4A through 4H.

Figure 4A:
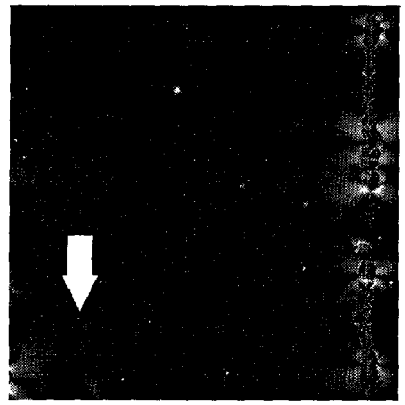
FIG. 4A is a scanned image of the optical appearance of a polyurethane replica on a glass substrate taken through a microscope with cross polarizers. The white arrow in the scanned image indicates the direction of grooves in the replica surface.
Figure 4B:
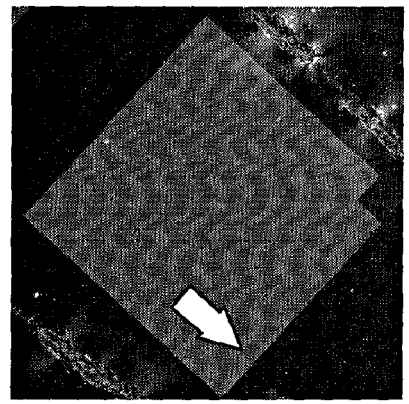
FIG. 4B is a scanned image of the optical appearance of the polyurethane replica of FIG. 4A taken through a microscope with cross polarizers where the replica is rotated by 45° with respect to one of the polarizers. The white arrow indicates the direction of grooves in the replica surface.

Polyurethane replica nanostructured substrates formed on glass supports are optically transparent. Therefore, light microscopy may be used to analyze the surface of these polymeric replicas over the whole area of the replicated grooved structure (1.8 mm×1.8 mm size). The grooved area could not be distinguished from the non-patterned area when the direction of groove was parallel to one of the polarizers as shown in FIG. 4A. However, polarized light was transmitted through the grooved area upon rotation of the polymeric replica. Maximum transmittance was achieved when the direction of the grooved pattern was rotated by about 45° with respect to the direction of one of the polarizers (FIG. 4B). In contrast, because the non-grooved area is isotropic, no difference in the amount of light transmitted through these areas occurred when the polymeric replica was rotated between crossed polarizers.

Figure 4C:
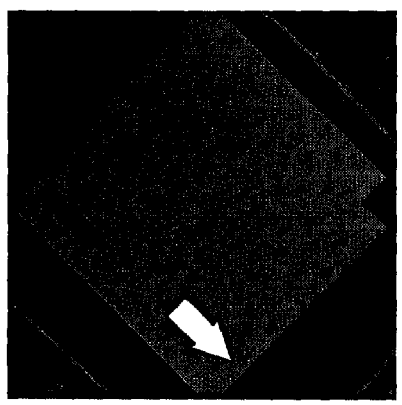
FIG. 4C is a scanned image of the optical appearance of a coated (12 nm Au on 3 nm Ti) polyurethane replica taken through a microscope with cross polarizers where the analyzer is rotated by 90° with respect to one of the polarizers. The white arrow indicates the direction of grooves in the replica surface.

As noted above, nanostructured substrates may be modified by depositing a thin film of a metal such as gold or silver on a top surface and then forming a SAM on it. For example, a uniform and thin layer of a metal (12 nm Au on 3 nm Ti) was deposited on the surface of a polyurethane replica nanostructured substrate using an e-beam evaporator. Anisotropic features were still readily observed using a polarized light microscope as shown in FIG. 4C although the anisotropy of the gold-coated replica was lower than that of the corresponding uncoated polyurethane replica (FIG. 4B).

Figure 4D:
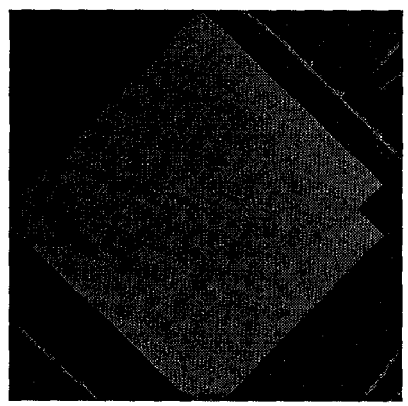
FIG. 4D is a scanned image of the optical appearance of a coated (12 nm Au on 3 nm Ti) polyurethane replica with a self-assembled monolayer formed from $HS(CH_2)_{11}COOH$ on the surface taken through a microscope with cross polarizers where the analyzer is rotated by 90° with respect to one of the polarizers.
Figure 4E:
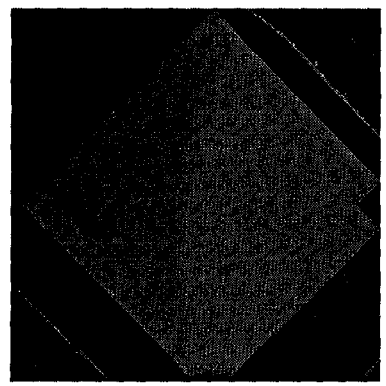
FIG. 4E is a scanned image of the optical appearance of a coated (12 nm Au on 3 nm Ti) polyurethane replica with a self-assembled monolayer formed from $HS(CH_2)_{11}COOH$ on the surface and a drop of hexadecane placed on the surface taken through a microscope with cross polarizers where the analyzer is rotated by 90° with respect to one of the polarizers.
Figure 4F:
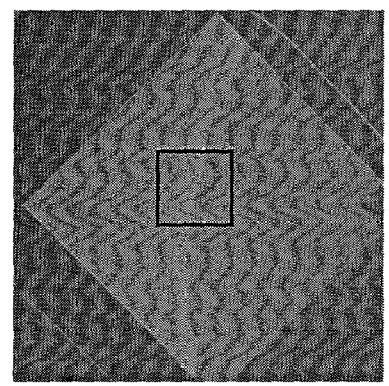
FIG. 4F is a scanned image of the optical appearance of the SAM-containing coated polyurethane replica of FIG. 4E with hexadecane where the analyzer is rotated by 91° with respect to one of the polarizers.

A nanostructured substrate that includes a hydrophilic SAM was formed on a gold-coated polyurethane replica nanostructured substrate by contacting the gold-coated substrate with an ethanolic solution of $HS(CH_2)_{10}COOH$. The optical appearance of the SAM-containing gold-coated polyurethane replica as viewed through a light microscope using cross polarizers is shown in FIG. 4D. A drop of hexadecane placed on the right portion of the top surface could easily be imaged on the top surface of the SAM-containing gold-coated nanostructured substrate. As shown in FIG. 4E, the drop of hydrocarbon was readily observed on the nanostructured substrate. Slight rotation of the analyzer (a change in 1°) with respect to the crossed polarizers dramatically increased the contrast of the optical image generated by the hexadecane drop on the surface as shown in FIG. 4F. Because the transmission of monochromic light through the analyzer in isotropic media (i.e., non-grooved area) is minimum between crossed polarizers, the difference in the intensity of passed light between the grooved and non-grooved areas becomes maximum when the groove direction of the replica is rotated by 45° with respect to one of the polarizers of the cross polarizers. When white light was used, however, the variation in retardation color caused by passage of light through the anisotropic media (i.e., grooved pattern) enhanced the distinction of its image from that of non-grooved area. In other words, modulating the retardation color by slightly rotating the analyzer (less than 1° to about 2°) increased the optical contrast of the anisotropic image increased (see FIGS. 4E and 4F) even though the percent difference in the intensity of light passed between the grooved and non-grooved areas decreased compared with crossed polarizers.

As noted above and demonstrated in FIGS. 4D-4G, the drop of hexadecane was readily imaged in the grooved area of the nanostructured substrate. However, hexadecane was not detectable in the non-grooved region because the hexadecane (n=1.4340) did not replace the air (n=1) in the non-grooved portion of the nanostructured substrate as it did in the grooved portion. Therefore, no resulting change in the optical properties of the non-grooved region occurred whereas a substantial change occurred in the region with grooves.

Figure 4G:
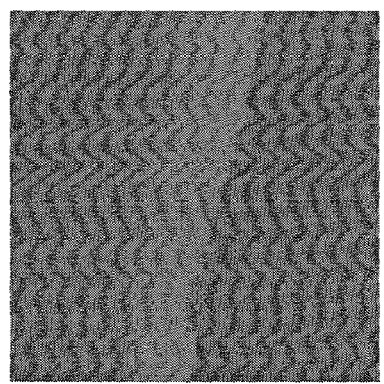
FIG. 4G is a 5× magnified view of the area in the square shown in FIG. 4F.
Figure 4H:
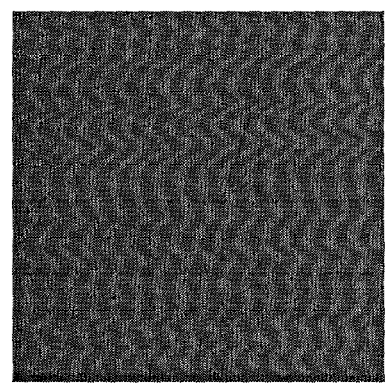
FIG. 4H is a 5× magnified view of the optical appearance of the SAM-containing coated polyurethane replica corresponding to that shown in FIG. 4G when viewed without cross polarizers.

The image of the bulk hexadecane drop on the grooved area of the SAM-containing gold-coated polyurethane replica is represented by the dark area on the right side of FIG. 4G. When viewed in color, the dark area of the bulk hexadecane drop was pink. The lighter area just to the left of the dark hexadecane drop area represents a boundary thin line. The lighter area was light yellow, and the area to the left of the light yellow area was light blue allowing the difference between the light yellow region and the light blue region to be more readily visualized in color. When the drop of hexadecane was placed on the grooved surface of the nanostructured substrate, preferential flow of the hexadecane boundary thin line (lighter area) was followed by bulk flow of the hexadecane (dark area) in the direction of the grooves. It is assumed that the nanogrooves in the substrate surface induced the flow of liquid in the same manner in which channel flow is caused by narrow grooves of rough surfaces and that the advanced thin layer represented by the lighter area corresponds to the presence of the precursor film. The role of the precursor film in the wetting process of a droplet on a solid substrate has been considered a dominant phenomena in the spreading mechanism. Ellipsometry measurements by others have shown that the spreading droplet advances as a series of distinct molecular layers. Heslot, F., Fraysse, N. and Cazabat, A. M. "Molecular Layering in the Spreading of Wetting Liquid Drops", Nature, 338, pp 640-642 (1989). Without being limited by conjecture, it is hypothesized that the advancing thin precursor film of hexadecane incompletely filled the grooves in the nanostructured substrate thereby generating different retardation compared to the bulk hexadecane in which the grooves were completely filled with hexadecane. The difference in retardation explains the difference in the appearances of the optical texture between the areas of bulk liquid and advanced precursor film represented by the dark and lighter areas in FIG. 4G. When the cross polarizers were removed, no evidence of the precursor film was observed (see FIG. 4H). Furthermore, in the absence of cross polarizers, the boundary of the bulk hexadecane was only slightly observed as shown in FIG. 4H.

Retardation Effects of Gold

Figure 5:
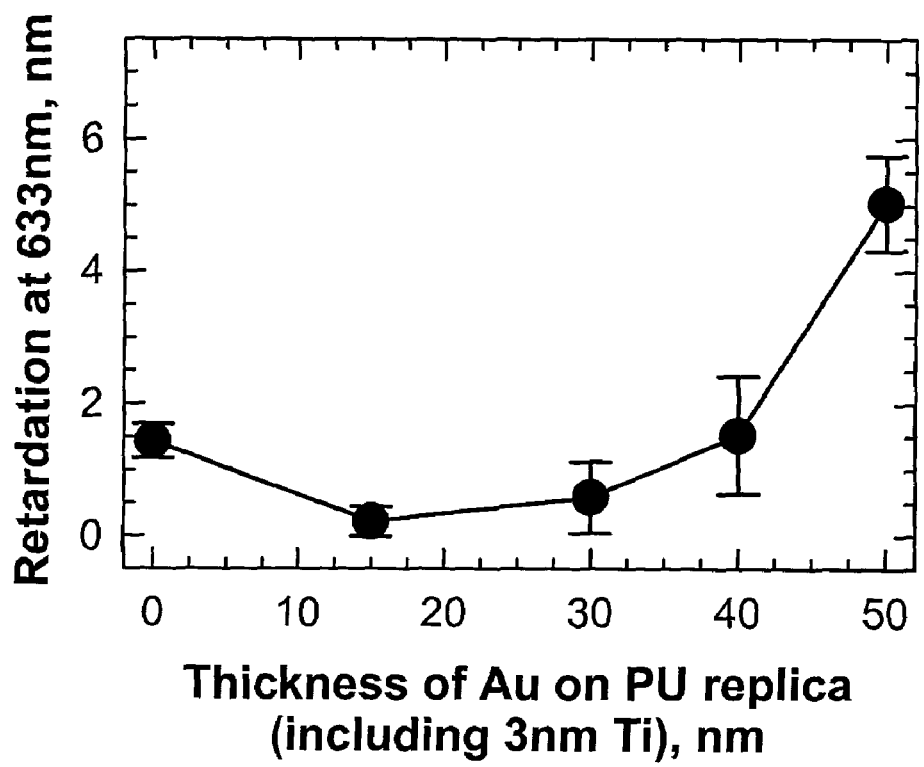
FIG. 5 is a graph of the retardation of gold-coated polyurethane replicas (with 3 nm Ti) on a glass substrate measured by using a compensator (filled circles) as a function of the thickness of the gold layer on the replica surface where the wavelength of passed light is 633 nm obtained by filtering white light through an interference filter.

In order to determine what role metals such as gold play on the anisotropy properties of metallized nanostructured substrates, retardation was measured as a function of the thickness of the gold deposited on a polyurethane nanostructured substrate surface (FIG. 5). Retardation was determined using a Brace-Köhler compensator (measuring range: 0-1/30 λ) filtering a white light source with a polarized light microscope (interference filter of 632.8 nm, full width at half-maximum: 10 nm). Even though AFM analysis indicated that the surface morphology of the SWG was not significantly modified by coating the replica with gold and titanium (see FIGS. 1A, 1B, 2A, 2B, 3A, and 3B) complex trends in the optical properties were found to depend on the thickness of gold layer. For example, a thin layer of gold of less than about 20 nm caused a decrease in retardation whereas a film of gold with a thickness greater than about 20 nm resulted in increased retardation (see FIG. 5).

Surface Plasmon Effects of Metallization

Figure 7:
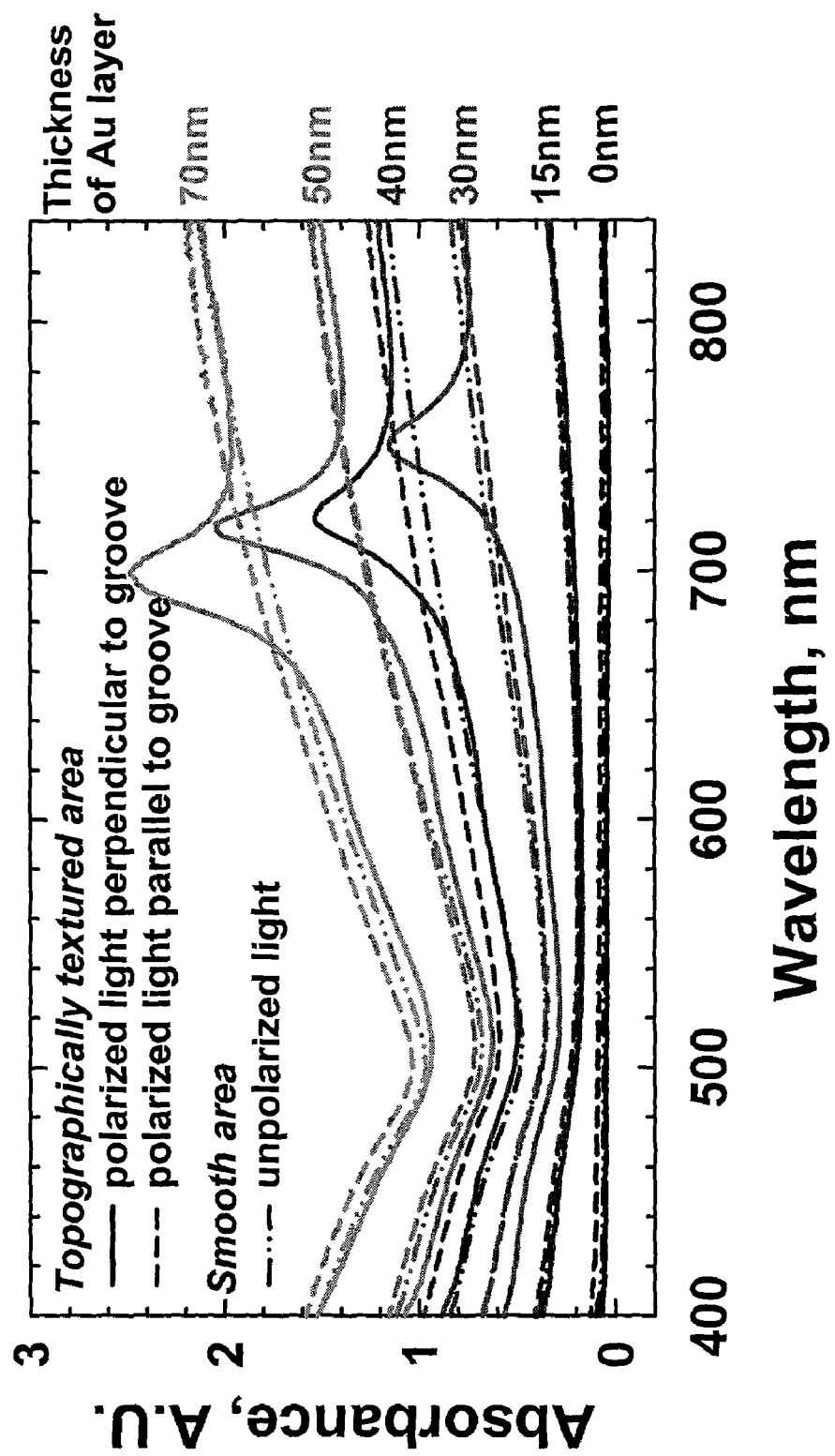
FIG. 7 is a graph of the absorbance of gold-coated polyurethane replicas measured as a function of wavelength when using polarized or unpolarized light.

In order to further explore the role that metals such as gold or silver play on the anisotropic properties of metallized nanostructured substrates, the optical absorption of the substrates was measured as a function of the polarization and wavelength of the light. The absorbance spectra of the substrates were obtained using a UV-VIS spectrometer (Cary 1E, Varian, Inc., Tempe, Ariz.). Because the topographically textured area is small (1.8 mm×1.8 mm), the sample holder which contained the glass slides was wrapped completely with aluminum foil except for a small hole (1 mm×1 mm) to transmit the light, and the topographically textured area or smooth area of polymeric substrate was secured onto the small transparent hole in the sample holder using Scotch® brand adhesive tape. Polarized light was obtained by placing a dichroic sheet polarizer (Melles Griot, Irvine, Calif.) in front of the light source of the spectrometer. As shown in FIG. 7, when a planar substrate that included a metallized gold top surface was used, no measurable plasmon absorption (peak around 700-750 nm) was observed when using light that included all polarizations. When using a non-metallized polyurethane replica, there was no plasmon absorption for either polarizations of the incident light (parallel or perpendicular to grooves). In contrast, when a polyurethane replica was coated with gold having a thickness greater than 15 nm, the appearance of a plasmon absorption peak at approximately 750 nm was evident when using polarized light with a plane of polarization that was perpendicular to the grooves. The absorption was measured at normal incidence. As shown in FIG. 7, as the thickness of the metal in the metallized top surface of the substrate increased, the plasmon absorption moved to shorter wavelengths (approximately 700 nm).

Detecting an Analyte Using Surface Plasmon Absorbance

A gold coated (50 nm Au on 3 nm Ti) polyurethane replica prepared as described above was immersed in a solution of BSA. Biotinylated BSA was deposited on the substrate by immersion of the substrate into a 1 mg/mL phosphate buffered saline (PBS) solution of biotinylated BSA for 2 hours. The substrate was then rinsed with PBS. A droplet of anti-BSA IgG (2 µM in PBS) was then deposited onto one part of the BSA-coated replica, incubated for 2 hours, and then rinsed with deionized water and dried under a gaseous stream of nitrogen. A second drop of anti-goat IgG (2 µM in PBS) was incubated on the other side of the replica for two hours. The substrate was then placed onto a polarized light microscope and viewed in transmission with the analyzer removed from the optical path. The incident light had a wavelength of 700 nm and was obtained by passing white light through an interference filter. The optical appearance of the replica was observed as a function of the polarization of the incident light. When the polarization of the incident light was perpendicular to the groove of the replica, the regions of the replica that possessed topography were darker (high absorbance of polarized light) than the areas of the replica that did not possess topography. In contrast, when the polarization of the incident light was parallel to the grooves of the replica, the region of the replica that possessed topography were lighter than the surrounding regions that did not possess topography. The dependence of the contrast on the incident polarization of light is consistent with the presence of the plasmon absorbance. In addition, when viewed with light having a wavelength of 633 nm, the above described dependence of absorbance on polarization and topography was not observed (no plasmon absorbance at 633 nm). When the region of the substrate contacted with anti-BSA IgG were inspected using light with a polarization perpendicular to the grooves, these regions were found to be brighter than the regions not contacted with and not supporting anti-BSA IgG. This contrast was substantially lost when the polarization of the incident light was parallel to the grooves (no plasmon absorption) or the wavelength of the incident light was 633 nm (no plasmon absorbance).

Preparation of BSA-Coated Nanostructured Substrate and Interaction of Substrate with Anti-BSA IgG and Anti-Goat IgG Biotinylated BSA was deposited on a substrate by immersion of the substrate into a 1 mg/mL phosphate buffered saline (PBS) solution of biotinylated BSA for 2 hours. The substrate was then rinsed with PBS. A droplet of anti-BSA IgG (2 micromolar in PBS) was then deposited onto one part of the BSA-coated replica, incubated for 2 hours, and then rinsed with deionized water and dried under a gaseous stream of nitrogen. A second drop of anti-goat IgG (2 micromolar in PBS) was incubated on the other side of the replica for two hours.

Figure 6A:
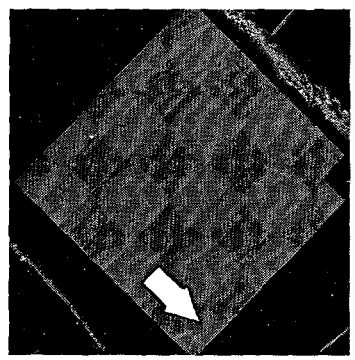
FIG. 6A is a scanned image of the optical appearance of a coated (47 nm Au on 3 nm Ti) polyurethane replica on a glass substrates viewed through a microscope with cross-polarizers after incubation in a 2 mg/mL BSA phosphate-buffered saline (pH of 7.4) solution for 2 hours.
Figure 6B:
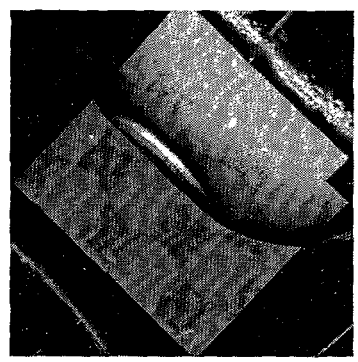
FIG. 6B is a scanned image of the optical appearance of the BSA and Au/Ti-coated polyurethane replica of FIG. 6A showing a drop of a 2 µM anti-BSA IgG phosphate-buffered saline solution placed on the surface.
Figure 6C:
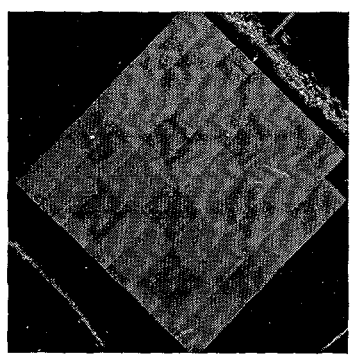
FIG. 6C is a scanned image of the optical appearance of the replica shown in FIG. 6B after removing the drop of anti-BSA IgG, rinsing the replica with deionized water, and drying the replica with nitrogen. The drop of anti-BSA IgG solution remained on the surface of the replica for 2 hours before removal.

As indicated above, the coating of a nanostructured substrate with a secondary material such as gold or titanium changed the optical properties of a nanostructured substrate formed of polyurethane on glass as imaged through polarized light. Other coating materials produced similar changes. For example, the binding of an analyte on the surface of a substrate bearing a receptor species caused a change in the optical properties of the substrate. For this reason, nanostructured substrates that include receptor molecules may be used to detect the presence of an analyte that binds the receptor in a sample without requiring the use of a liquid crystal for visualization. The optical appearance of a BSA-coated metallized (47 nm Au on 3 nm Ti) polyurethane replica nanostructured substrate viewed through cross polarizers using a light microscope is shown in FIG. 6A. The BSA-coated substrate was prepared by incubating the metallized (47 nm Au on 3 nm Ti) polymeric replica in a BSA (1 mg/1 mL) phosphate buffered saline (PBS) solution for 2 hours. Ellipsometric measurements obtained assuming a uniform, planar coating of gold showed an increase in thickness of about 2.6+/−0.1 nm produced by adsorption of the BSA. A drop of an anti-BSA IgG (2 µM) PBS solution was placed on one part of the BSA-coated substrate prepared as described above. The drop of the anti-BSA IgG solution is shown in FIG. 6B as viewed through a microscope using cross polarizers. After contacting the substrate for 2 hours, the anti-BSA IgG solution was removed, and the substrate was rinsed with deionized water and dried under a stream of nitrogen. FIG. 6C shows the optical appearance of the substrate viewed through a microscope using cross polarizers after this procedure had been accomplished. The portion of the substrate that was contacted with the anti-BSA IgG was clearly evident as indicated by the brighter portion of the substrate in the black and white image. The difference in the regions was even more evident when viewed in color.

Figure 6D:
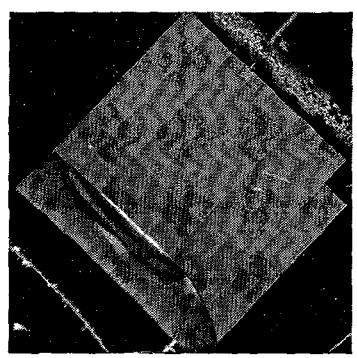
FIG. 6D is a scanned image of the optical appearance of the polyurethane replica of FIG. 6C showing a drop of a 2 µM anti-goat IgG phosphate-buffered saline solution placed on the surface of the replica shown in FIG. 6C.
Figure 6E:
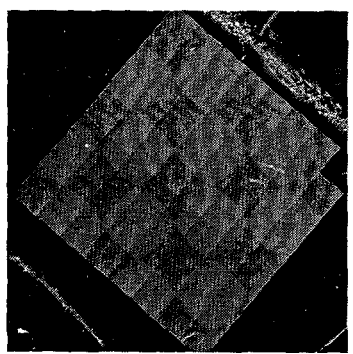
FIG. 6E is a scanned image of the optical appearance of the replica shown in FIG. 6D after removing the drop of anti-goat IgG, rinsing the replica with deionized water, and drying the replica with nitrogen. The drop of anti-goat IgG solution remained on the surface of the replica for 2 hours before removal.

The BSA-coated metallized (47 nm Au on 3 nm Ti) polyurethane replica nanostructured substrate that had previously been contacted with the anti-BSA IgG and was imaged in FIG. 6C was next contacted with anti-goat IgG to determine whether the substrate would show any change in optical properties with a protein that should not bind to the BSA. A drop of an anti-goat IgG (2 µM) PBS solution was placed on the BSA-coated substrate in an area that had not been contacted with the anti-BSA IgG. The drop of the anti-goat IgG solution is shown in FIG. 6D as viewed through a microscope using cross polarizers. After contacting the substrate for 2 hours, the anti-goat IgG solution was removed, and the substrate was rinsed with deionized water and dried under a stream of nitrogen. FIG. 6E shows the optical appearance of the substrate as viewed through a microscope using cross polarizers after the anti-goat IgG had been removed and the substrate had been rinsed and dried. As shown in FIG. 6E, no noticeable change in the optical image resulted from contact with the non-specific anti-goat IgG. These results indicate that the BSA did not bind the anti-goat IgG and acted as a blocking layer for this material while acting as a receptor species for the anti-BSA IgG.

Figure 6F:
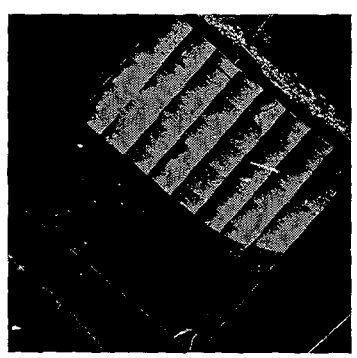
FIG. 6F is a scanned image of the optical appearance of the replica shown in FIG. 6E after the contrast has been amplified by adjusting the contrast and brightness of the image.

Ellipsometric thickness measurements provided indirect information about the binding of specific (anti-BSA IgG) and non-specific (anti-goat IgG) IgGs on the BSA-coated nanostructured substrate surface. The biotinylated BSA was deposited on the substrate by immersion of the substrate into a 1 mg/mL PBS solution of biotinylated BSA for 2 hours. The substrate was then rinsed with PBS. A droplet of anti-BSA IgG (2 micromolar in PBS) was then deposited onto one part of the BSA-coated replica, incubated for 2 hours, and then rinsed with deionized water and dried under a gaseous stream of nitrogen. A second drop of anti-goat IgG (2 micromolar in PBS) was incubated on the other side of the top surface of the replica for two hours. Specific binding by anti-BSA IgG resulted in a large increase in the ellipsometric thickness of about 7.5 nm+/−0.5 nm as expected. In direct contrast, non-specific binding by anti-goat IgG resulted in only a small increase in ellipsometric thickness of about 0.8 nm+/−0.2 nm. Manipulation of the captured image was accomplished by changing the contrast and brightness with a graphics program, and the enhanced image provided enhanced optical resolution showing specific binding by the anti-BSA IgG (FIG. 6F). These results indicate that nanostructured substrates with specific receptor molecules may be used in field assays and bioassays to determine the presence of an analyte in a particular sample. The change in the optical image produced by binding of analyte to receptor may be directly observed without requiring additional steps such as secondary antibody or fluorescent label. Furthermore, the presence of analytes and the detection of surface phenomena may be observed without requiring the use of liquid crystal in the visualization process.

Preparation of A Nanostructured Substrate with a BSA Blocking Layer and a Different Receptor Species A gold coated substrate is immersed in an ethanol solution (1 mM) of aminopropylmercaptan for 1 hour, rinsed with ethanol, and then dried. The surface is activated by immersing the resulting substrate in a 1 mM dimethylsulfoxide solution of disuccinimidyl suberate for 2 hours. The activated surface is next contacted with a droplet of PBS solution of anti-Ras IgG (10 micromolar) for 4 hours. The resulting surface is then rinsed in PBS and immersed completely in a 1 mg/mL solution of BSA. To detect the presence of Ras in a solution, the substrate is immersed in the solution for 6 hours. The substrate is removed, rinsed in PBS, rinsed in water, and then is dried under a stream of nitrogen. The substrate is then placed in a polarized light microscope. The substrate is imaged using a CCD camera. Optical contrast between the region of the surface that contacted the anti Ras IgG and the surrounding region indicates the presence of Ras in the sample.

The form birefringence is generated by SWG structures of isotropic materials. In order to determine whether a polyurethane replica nanostructured substrate possessed additional optical properties such as birefringence generated by material anisotropy, the optical appearance of the polyurethane substrate was observed where the SWG surface of the polyurethane replica was covered with a thin film of a nematic liquid crystal (isotropic 4-cyano-4'-pentylbiphenyl, (5CB). Because 5CB has a refractive index of approximately 1.58 in its isotropic phase (approximately 40° C.), it could be matched with the refractive index of polyurethane (approximately 1.56). Erasure of the anisotropy in the polyurethane replica occurred due to filling the SWG surface with isotropic 5CB. These results indicate that the anisotropic images of the polyurethane replicas resulted from form birefringence resulting solely from the SWG structure.

It is understood that the invention is not limited to the embodiments set forth herein for illustration, but embraces all such forms thereof as come within the scope of the claims.

What is claimed is:

1. A method for imaging a phenomenon that occurs on a surface of a substrate, comprising:
   (a) contacting a fluid with a top surface of a substrate, the top surface of the substrate comprising an anisotropic topography and defining a plurality of grooves, the grooves having a width ranging from 1 nm to 1,000 nm and a depth ranging from 1 nm to 5,000 nm, wherein the grooves are separated by a distance ranging from 1 nm to 5,000 nm; and (b) imaging a phenomenon that occurs on the top surface of the substrate by observing the substrate through incident and transmitted polarized light in the absence of a liquid crystal after the fluid has contacted the top surface of the substrate, wherein the wavelength of the polarized light is larger than the width and/or separation of the grooves defined on the top surface of the substrate;

wherein the substrate is observed using a polarizer and an analyzer.

2. The method of claim 1, wherein the substrate comprises a polymer.

3. The method of claim 2, wherein the substrate comprises polyurethane.

4. The method of claim 2, wherein the substrate further comprises a glass support underlying the polymer.

5. The method of claim 1, wherein the width of the grooves defined by the top surface of the substrate ranges from 10 nm to 400 nm.

6. The method of claim 1, wherein the depth of the grooves defined by the top surface of the substrate ranges from 10 nm to 400 nm.

7. The method of claim 1, wherein the grooves defined by the top surface of the substrate are separated by a distance ranging from 10 nm to 400 nm.

8. The method of claim 1, wherein the grooves are parallel.

9. The method of claim 1, wherein the top surface of the substrate is coated with a metal.

10. The method of claim 9, wherein the metal is gold or silver, and the metal coated on the top surface of the substrate has a thickness ranging from 1 nm to 500 nm.

11. The method of claim 1, wherein the analyzer is configured so that it ranges from 0.5° from a crossed configuration to 5° from a crossed configuration.

12. The method of claim 1, wherein the grooves defined by the top surface of the substrate have a width ranging from 10 nm to 400 nm and a depth ranging from 10 nm to 400 nm, and wherein the grooves are separated by a distance ranging from 10 nm to 400 nm.

13. The method of claim 1, wherein the polarized light comprises a wavelength ranging from 600 nm to 850 nm.

14. A method for imaging a phenomenon that occurs on a surface of a substrate, comprising:

(a) contacting a fluid with a top surface of a substrate, the top surface of the substrate comprising an anisotropic topography and defining a plurality of grooves, the grooves having a width ranging from 1 nm to 1,000 nm and a depth ranging from 1 nm to 5,000 nm, wherein the grooves are separated by a distance ranging from 1 nm to 5,000 nm; and (b) observing a change in a polarization of transmitted light by observing the substrate in the absence of a liquid crystal on the substrate before and after the fluid has contacted the top surface of the substrate, wherein the wavelength of the polarized light is larger than the width and/or separation of the grooves defined on the top surface of the substrate.

15. The method of claim 14, wherein the observing a change in a polarization of light is performed with a polarizer and an analyzer configured to range from a crossed configuration to a configuration within 10° of a crossed configuration.

16. The method of claim 15, wherein the analyzer is configured so that it ranges from 0.5° from a crossed configuration to 5° from a crossed configuration.

17. The method of claim 14, wherein the grooves defined by the top surface of the substrate have a width ranging from 10 nm to 400 nm and a depth ranging from 10 nm to 400 nm, and wherein the grooves are separated by a distance ranging from 10 nm to 400 nm.

18. The method of claim 14, wherein a first portion of the top surface of the substrate comprises a receptor molecule that binds to an analyte.

19. The method of claim 18, wherein the substrate further comprises a polymer and wherein the top surface of the substrate further comprises a metal coating, wherein the receptor molecule is deposited over a self-assembled monolayer formed from an organ sulfur compound on a top surface of the metal coating.

20. The method of claim 19, wherein the organ sulfur compound is a compound having the formula $HS(CH_2)_m CO_2H$ wherein m is an integer having a value of 6, 7, 8, 9, 10, 11, 12, 13, 14, 15, 16, 17, or 18.

21. The method of claim 18, wherein the top surface of the substrate further comprises a blocking layer comprising a serum albumin.

22. The method of claim 21, wherein the blocking layer comprises bovine serum albumin.

23. The method of claim 18, wherein the receptor molecule is selected from the group consisting of a peptide, a polypeptide, a protein, a fragment of RNA, a fragment of DNA, a drug, a growth factor, a cytokine, a low molecular weight molecule, a member of a library of organic compounds, biotin, avidin, a sugar, a polysaccharide, an immunoglobulin, and a fragment of an immunoglobulin.

24. The method of claim 18, wherein the analyte is selected from the group consisting of a protein, a virus, a prokaryotic organism, a eukaryotic organism, a molecule, an ion, DNA, RNA, a fragment of DNA, a fragment of RNA, and a peptide.

25. The method of claim 14, wherein the top surface of the substrate comprises a plurality of different receptor molecules.

26. The method of claim 14, wherein the polarized light comprises a wavelength ranging from 600 nm to 850 nm.

27. The method of claim 1, wherein the polarizer and the analyzer are in a configuration that ranges from a crossed configuration to a within 10° of a crossed configuration.

* * * * *